United States Patent
Jagani et al.

(10) Patent No.: US 9,850,543 B2
(45) Date of Patent: Dec. 26, 2017

(54) BIOMARKERS ASSOCIATED WITH BRM INHIBITION

(71) Applicants: Zainab Jagani, Cambridge, MA (US); Gregory Hoffman, Cambridge, MA (US); Frank Peter Stegmeier, Cambridge, MA (US); Craig Stephen Mickanin, Cambridge, MA (US)

(72) Inventors: Zainab Jagani, Cambridge, MA (US); Gregory Hoffman, Cambridge, MA (US); Frank Peter Stegmeier, Cambridge, MA (US); Craig Stephen Mickanin, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/777,211

(22) PCT Filed: Mar. 12, 2014

(86) PCT No.: PCT/US2014/024128
§ 371 (c)(1),
(2) Date: Sep. 15, 2015

(87) PCT Pub. No.: WO2014/150751
PCT Pub. Date: Sep. 25, 2014

(65) Prior Publication Data
US 2016/0032402 A1    Feb. 4, 2016

Related U.S. Application Data

(60) Provisional application No. 61/791,945, filed on Mar. 15, 2013, provisional application No. 61/846,178, filed on Jul. 15, 2013.

(51) Int. Cl.
| | | |
|---|---|---|
| *A61K 31/70* | (2006.01) | |
| *C07H 21/02* | (2006.01) | |
| *C07H 21/04* | (2006.01) | |
| *C12Q 1/68* | (2006.01) | |
| *C12N 15/113* | (2010.01) | |
| *G01N 33/574* | (2006.01) | |
| *C12N 5/00* | (2006.01) | |

(52) U.S. Cl.
CPC ........ *C12Q 1/6886* (2013.01); *C12N 15/1137* (2013.01); *G01N 33/57496* (2013.01); *C12N 2310/14* (2013.01); *C12N 2310/531* (2013.01); *C12N 2320/30* (2013.01); *C12Q 2600/106* (2013.01); *C12Q 2600/156* (2013.01); *C12Q 2600/158* (2013.01); *C12Q 2600/178* (2013.01); *G01N 2333/914* (2013.01)

(58) Field of Classification Search
None
See application file for complete search history.

(56) References Cited

U.S. PATENT DOCUMENTS

| | | | |
|---|---|---|---|
| 8,658,211 B2 * | 2/2014 | Rozema | A61K 47/48176 424/486 |
| 2004/0259247 A1 * | 12/2004 | Tuschl | A61K 48/00 435/375 |
| 2010/0130527 A1 | 5/2010 | Lehrer et al. | |
| 2011/0033443 A1 | 2/2011 | Moran et al. | |
| 2011/0236903 A1 | 9/2011 | McClelland et al. | |
| 2016/0130663 A1 | 5/2016 | Kohno et al. | |

FOREIGN PATENT DOCUMENTS

| | | |
|---|---|---|
| WO | 20100059742 A1 | 5/2010 |
| WO | 2010065940 A1 | 6/2010 |
| WO | 2011132175 A2 | 1/2011 |
| WO | 2012174282 A2 | 12/2012 |

OTHER PUBLICATIONS

Rodriguez-Nieto et al., Massive parallel DNA pyrosequencing analysis of the tumor suppressor BRG1/SMARCA4 in lung primary tumors. Hum Mutat. Feb. 2011;32(2):E1999-2017.
Vachtenheim et al., SWI/SNF chromatin remodeling complex is critical for the expression of microphthalmia-associated transcription factor in melanoma cells. Biochem Biophys Res Commun. Feb. 12, 2010;392(3):454-9.
Schramedei et al., MicroRNA-21 targets tumor suppressor genes ANP32A and SMARCA4. Oncogene. Jun. 30, 2011;30(26)1975-85.
Hoffman et al., Functional epigenetics approach identifies BRM/SMARCA2 as a critical synthetic lethal target in BRG1-deficient cancers. Proc Natl Acad Sci U S A. Feb. 25, 2014;111(8)3128-33.
Shain, et al., The Spectrum of SWI/SNF Mutations, Ubiquitous in Human Cancers, PLOS ONE, Jan. 23, 2013; 8(1):e55119.1.
Haimann et al., Screening and association testing of common coding variation in steroid hormone receptor co-activator and co-repressor genes in relation to breast cancer risk: the Multiethnic Cohort, BMC Cancer Jan. 9, 2009:43.
Melaiu et al., "A review of transcriptome studies combined with data mining reveals novel potential markers of malignant pleural mesothelioma", Mutation Research 2012, 750:132-140.

* cited by examiner

*Primary Examiner* — Sean McGarry
(74) *Attorney, Agent, or Firm* — Hong-Van M. Le

(57) ABSTRACT

The invention provides methods of detecting cancer biomarkers, such as one or more SWI/SNF complex mutations, in order to determine a cancer subject's amenability to therapeutic treatment with a BRM inhibitor. Kits, methods of screening for candidate BRM inhibitors, and associated methods of treatment are also provided.

13 Claims, 22 Drawing Sheets

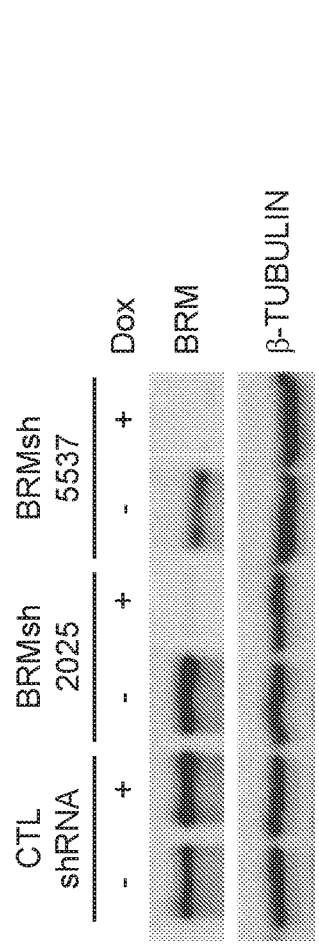
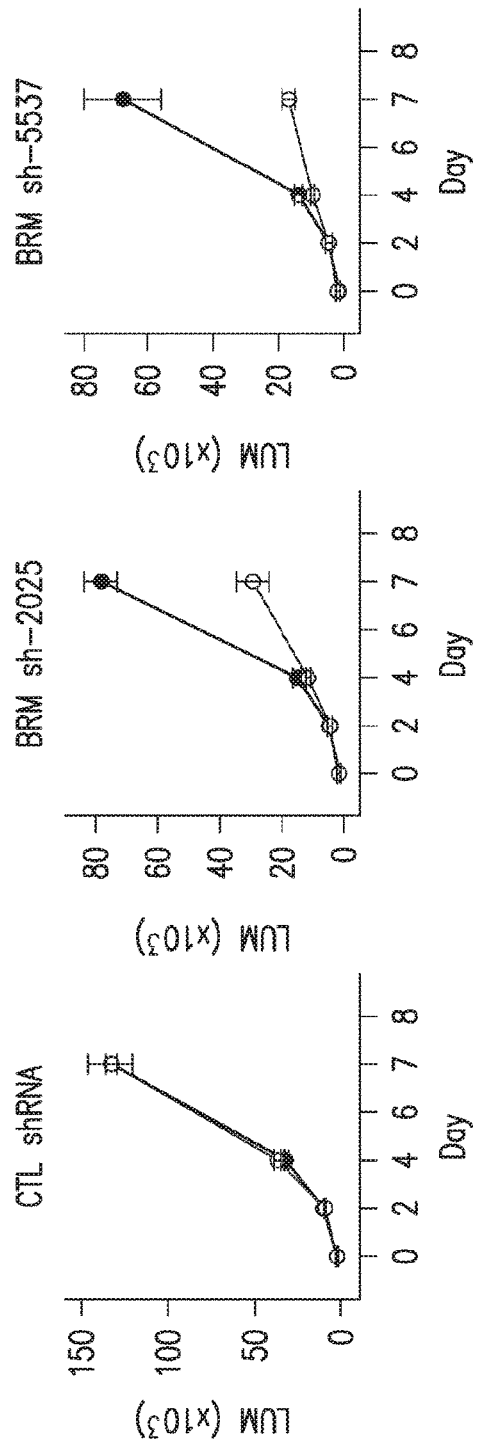
FIG.5A
FIG.5B

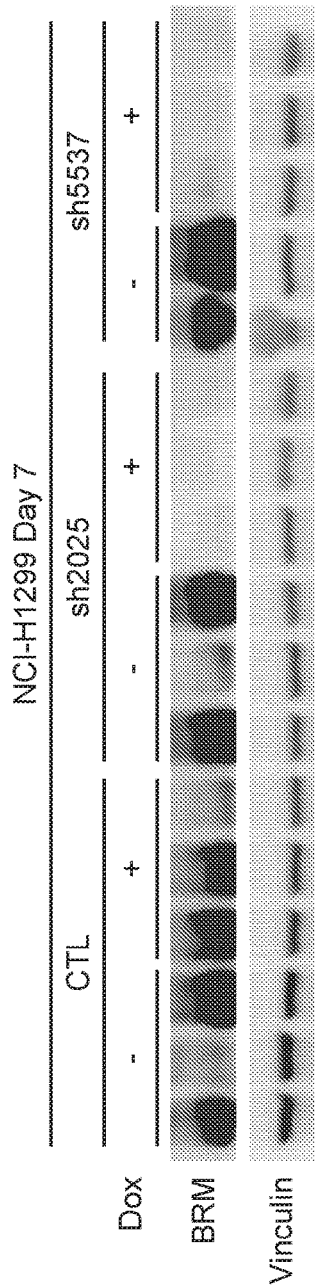
FIG. 8A
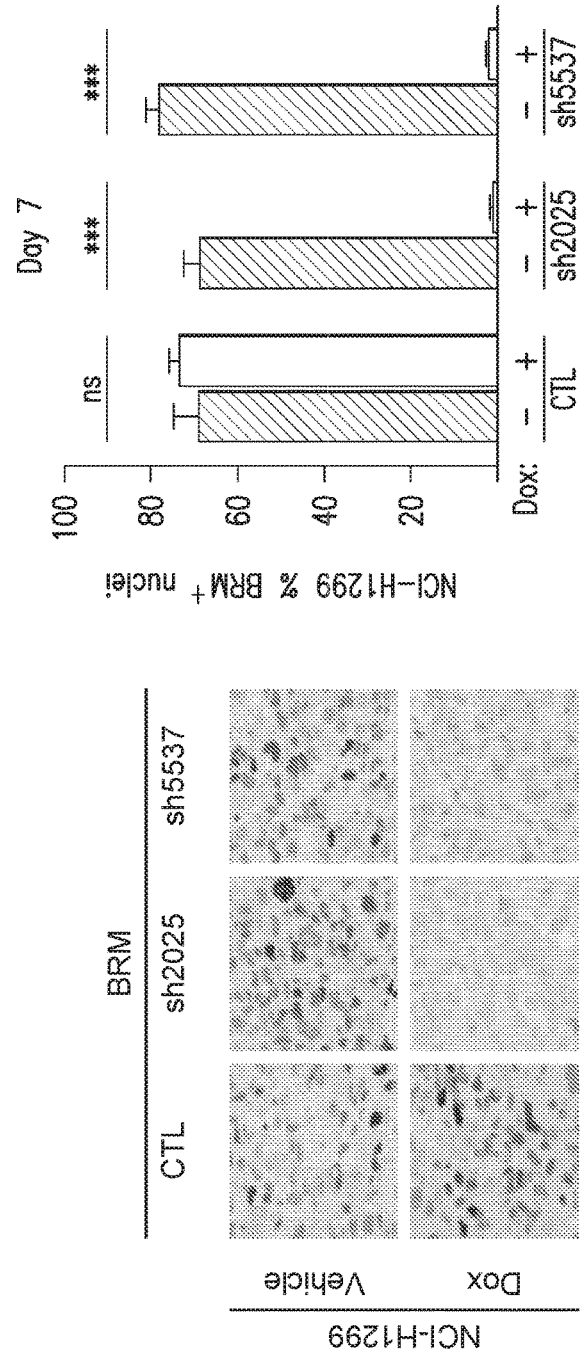
FIG. 8C
FIG. 8B

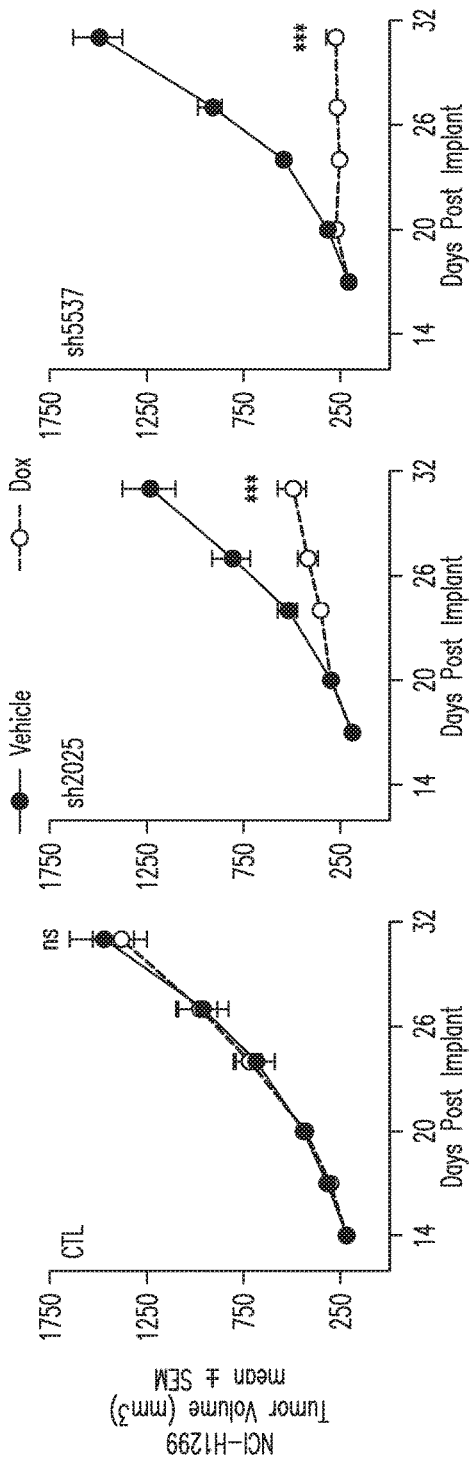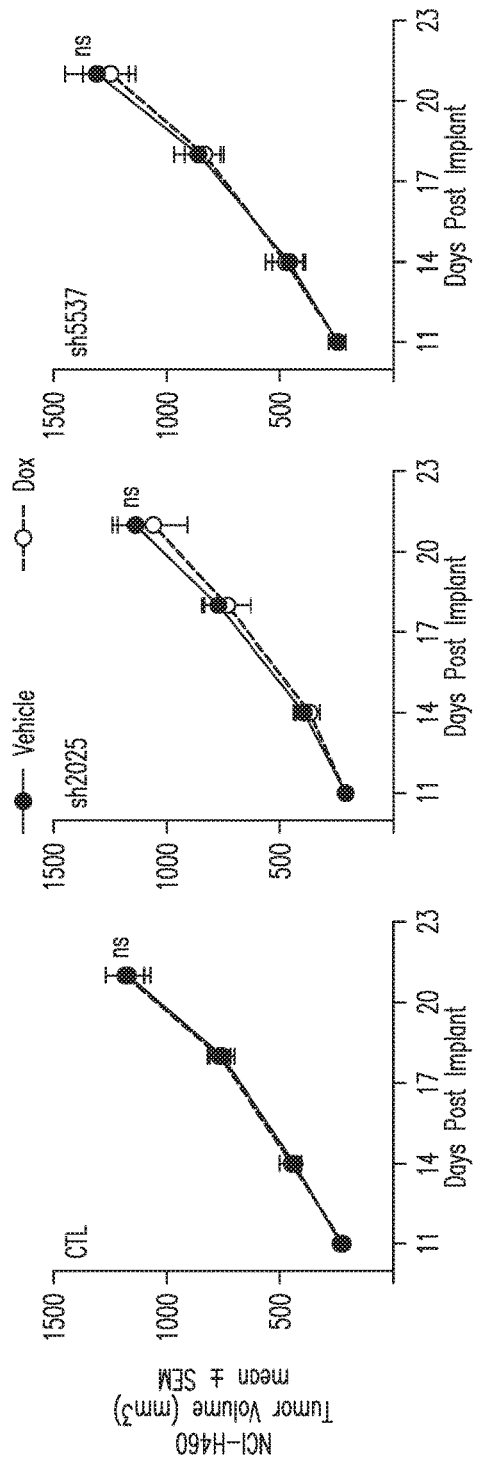
FIG. 8D
FIG. 8E

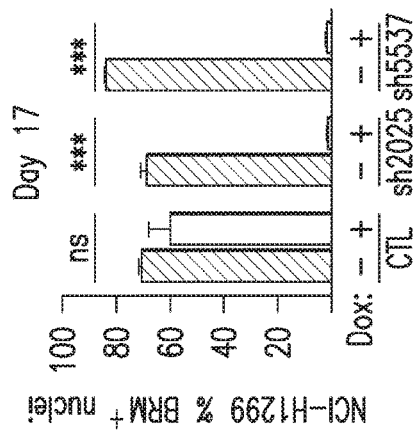
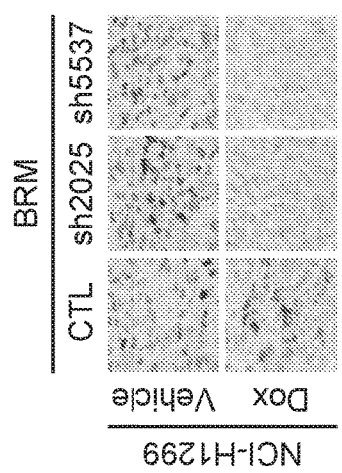
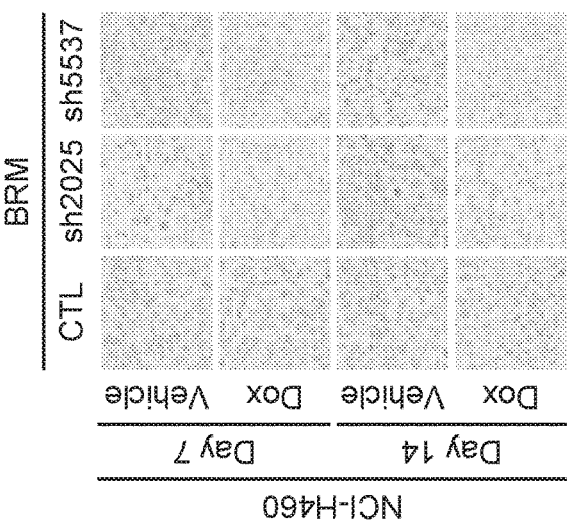

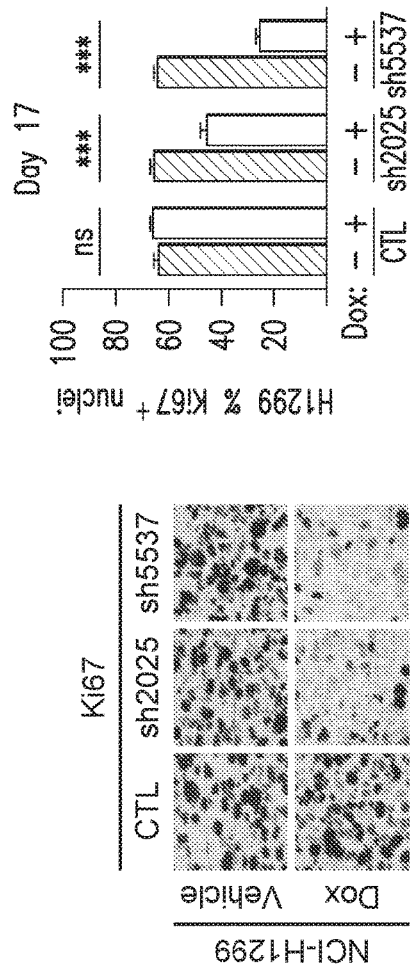
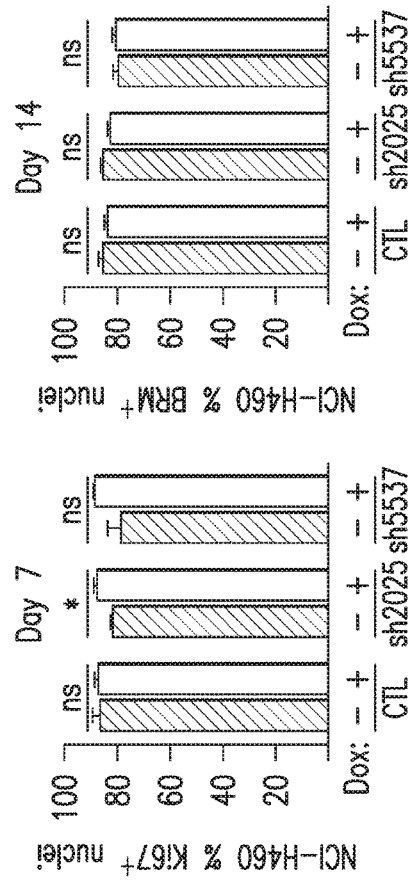
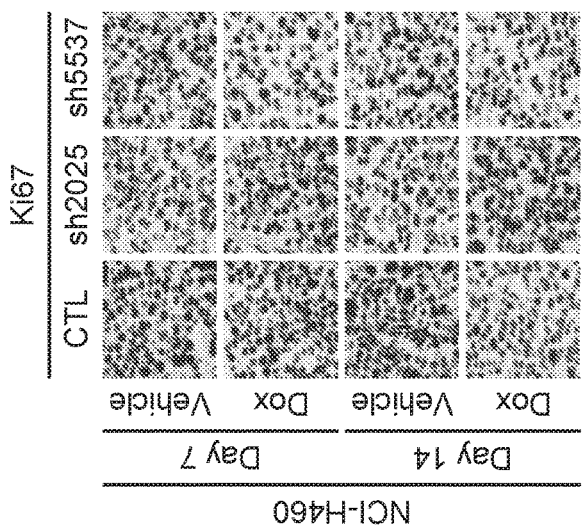

SEQUENCE LISTING

<160> NUMBER OF SEQ ID NOS: 22

<210> SEQ ID NO 1
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1
ccggggataa tggtgattga gatggctcga gccactcaat caccattatc cttttt    56

<210> SEQ ID NO 2
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 2
aattaaaaag gataatggtg attgagatgg ctcgagccac tcaatcacca ttatcc        56

<210> SEQ ID NO 3
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
ccgggaagag agtgattctg attatctcga gataatcaga atcactctct tcttttt       57

<210> SEQ ID NO 4
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 4
aattaaaaag aagagagtga ttctgattat ctcgagataa tcagaatcac tctcttc       57

<210> SEQ ID NO 5
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5
ccgggttgaa agcgctattg aatatctcga gatattcaat agcgctttca acttttt       57

<210> SEQ ID NO 6
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 6
aattaaaaag ttgaaagcgc tattgaatat ctcgagatat tcaatagcgc tttcaac       57

<210> SEQ ID NO 7
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 7
ccggcgactc tatctaactg gatatgttaa tattcatagc atgtccagtt agatagagtc    60
gtttttt    67

<210> SEQ ID NO 8
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
aattaaaaaa cgactctatc taactggata tgctatgaat attaacatgt ccagttagat    60
agagtcg    67

<210> SEQ ID NO 9
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ccggccaaac ttgtagtgag tgattgttaa tattcatagc aatcgctcac tacaggtttg    60
gtttttt    67

<210> SEQ ID NO 10
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
aattaaaaaa ccaaacttgt agtgagtgat tgctatgaat attaacaatc gctcactaca    60
ggtttgg    67

<210> SEQ ID NO 11
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
ccgggacagg tgtttagctt actttgttaa tattcatagc aaggtaagct aaacgcctgt    60
ctttttt    67

<210> SEQ ID NO 12
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
aattaaaaaa gacaggtgtt tagcttactt tgctatgaat attaacaagg taagctaaac    60
gcctgtc    67

<210> SEQ ID NO 13
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ccgggcagct aaagagaaga agagggttaa tattcatagc cttcttcttc tctttggctg    60
cttttt    67

<210> SEQ ID NO 14
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
aattaaaaaa gcagctaaag agaagaagag ggctatgaat attaaccttc ttcttctctt    60
tggctgc    67

<210> SEQ ID NO 15
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ccgggccaag caagatgtcg atgatctcga gatcatcgac atcttgcttg gctttttt    57

<210> SEQ ID NO 16
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
aattaaaaag ccaagcaaga tgtcgatgat ctcgagatca tcgacatctt gcttggc    57

<210> SEQ ID NO 17
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17

```
ggcagggata ttcaccatta tcgtttcaga                                      30

<210> SEQ ID NO 18
<211> LENGTH: 23
<212> TYPE: DNA
<213> ORGANISM: Homo sapiens

<400> SEQUENCE: 18
gcagtcctac tatgccgtgg ccc                                             23

<210> SEQ ID NO 19
<211> LENGTH: 17
<212> TYPE: DNA
<213> ORGANISM: Homo sapiens

<400> SEQUENCE: 19
cttgatagaa ttcttcc                                                    17

<210> SEQ ID NO 20
<211> LENGTH: 12
<212> TYPE: DNA
<213> ORGANISM: Homo sapiens

<400> SEQUENCE: 20
gaggagcagg at                                                         12

<210> SEQ ID NO 21
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
gttaatattc atagc                                                      15

<210> SEQ ID NO 22
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
gctatgaata ttaac                                                      15
```

US 9,850,543 B2

BIOMARKERS ASSOCIATED WITH BRM INHIBITION

FIELD OF THE INVENTION

The disclosure is directed to novel personalized therapies, kits, transmittable forms of information and methods for use in treating patients having cancer.

BACKGROUND OF THE INVENTION

The mammalian SWI/SNF (mSWI/SNF) multi-protein complexes regulate chromatin structure through ATP-dependent nucleosome remodeling and thereby control many key cellular processes (Wilson, B. G. and C. W. Roberts (2011). Nat Rev Cancer 11(7): 481-492). Several subunits of the mSWI/SNF complexes have roles as tumor suppressors, and recent genomic studies revealed recurrent mutations in several of these subunits, with a collective mutation frequency of approximately 20% across all cancers (Kadoch, C., Hargreaves, D. C., et al. (2013) Nat Genet. 45: 592-601). The catalytic SWI/SNF subunit BRG1, also known as SMARCA4, is frequently mutated in lung adenocarcinomas and other cancer types (Becker, T. M., S. Haferkamp, et al. (2009) Mol Cancer 8: 4.)(Imielinski, M., A. H. Berger, et al. (2012) Cell 150(6): 1107-1120).

The mechanisms by which mSWI/SNF mutations contribute to tumorigenesis remain poorly understood, and their inactivation presents a challenge for devising therapeutic strategies against these genetic lesions. Mutations in specific subunits of mSWI/SNF complexes are found in distinct cancer types. Overall, mSWI/SNF complexes have emerged as the most frequently mutated class of chromatin regulators in cancer; at least six subunits of the complex have been found to be specifically inactivated at high frequencies in cancers, including subsets of ovary, breast, kidney, lung, pancreas, uterus, bladder, stomach, colon, and liver (Kadoch, C., Hargreaves, D. C., et al. (2013) Nat Genet. 45: 592-601).

BRM (also known as SMARCA2) is the paralog of BRG1 (or BRM/SWI2-related gene 1, also known as SMARCA4), and these two proteins function as mutually exclusive ATP-dependent subunits within the mammalian SWI/SNF chromatin remodeling complex. Either BRM or BRG1 is required for cells to assemble a catalytically active SWI/SNF complex. Multiple variants of the SWI/SNF complex have been characterized with differing subunit composition, but only one catalytic subunit (BRM or BRG1) is present in each complex.

BRG1 has been shown to function as a tumor suppressor and is significantly mutated in human cancers (Medina, Romero et al. 2008; Becker, Haferkamp et al. 2009). Evidence for the tumor suppressive function of BRG1 has been demonstrated by re-expression of wild type BRG1 in BRG1-mutant cell lines, resulting in differentiation and cell cycle arrest (Hendricks, K. B., F. Shanahan, et al. (2004) Mol Cell Biol 24(1): 362-376, Dunaief, J. L., B. E. Strober, et al. (1994) Cell 79(1): 119-130). Brg1+/− mice develop mammary carcinoma with a 10% incidence in one year (Bultman, S. J., J. I. Herschkowitz, et al (2008) Oncogene 27(4): 460-468). Loss-of-function mutations in BRG1 have been identified in ~30% of established non-small-cell lung cancer lines, and silencing of BRG1 is found in many other cancer cell lines and tumor samples, including lung, pancreatic, and ovarian cancers, melanomas, and pediatric rhabdoid sarcomas (Wilson et al.; Roberts et al.). Importantly, recent results from the Cancer Genome Atlas (TCGA) project identified BRG1 mutations as one of the most prominent mutations in tumor samples from patients with lung adenocarcinoma, occurring in ~10% of all tumor samples (a rate similar to other well characterized oncogenes and tumor suppressors such as EGFR and LKB1)(Imielinski et al. (2012) Cell 150(6): 1107-1120). Therefore, identifying the key synthetic lethal nodes in mSWI/SNF mutant cancers, such as in BRG1-mutant/deficient cancers will be critical towards developing the appropriate therapeutic strategies for targeting such cancers.

There is an increasing body of evidence that suggests a patient's genetic profile can be determinative to a patient's responsiveness to a therapeutic treatment. Given the numerous therapies available to an individual having cancer, a determination of the genetic factors that influence, for example, response to a particular drug, could be used to provide a patient with a personalized treatment regime. Such personalized treatment regimens offer the potential to maximize therapeutic benefit to the patient while minimizing related side effects that can be associated with alternative and less effective treatment regimens. Thus, there is a need to identify factors which can be used to predict whether a patient is likely to respond to a particular therapy. It is of particular interest to determine predictive factors in the field of cancer biology, and to therapeutically exploit discoveries pertaining to key synthetic lethal nodes in the various SWI/SNF mutant cancers.

SUMMARY OF THE INVENTION

The invention is based on the identification of a novel synthetic lethal relationship between the catalytic mSWI/SNF subunits BRM and BRG1, from pooled short hairpin RNA (shRNA) screens of the human epigenome. Specifically, the invention is based on the novel finding that inhibition of BRM function blocks the growth of cancer cells with impaired or loss of BRG1 function due either to inactivating mutations in the BRG1 gene or loss of BRG1 expression through alternative mechanisms other than inactivating mutations. The invention represents a significant advance over current knowledge in the field, as no synthetic lethal interactions have been systematically identified with BRG1 mutation status to date ("synthetic lethality," as meaning when a combination of mutations in two or more genes leads to reduced cell viability and/or a reduced rate of cell proliferation, whereas a mutation in only one of these genes does not). As BRM is the paralog of BRG1, the discovery suggests a model wherein BRG1 mutations lead to a hypomorphic complex that promotes tumorigenesis, and wherein cancer cells cannot tolerate complete inactivation of the complex. Thus, targeting mSWI/SNF subunits that exhibit redundant activities to the mutated complexes, e.g., targeting BRM and BRG1, may present a general strategy for diagnosing and/or treating mSWI/SNF mutated cancers.

In one aspect, the invention includes a method for analyzing, evaluating, and/or detecting BRG1 mutation status, BRG1 gene expression levels, BRG1 protein levels in parallel to BRM expression status, and/or BRG1 protein function, to predict whether a subject afflicted with cancer associated with a BRG1 mutation will respond to therapeutic treatment with a BRM inhibitor. Analysis, evaluation, and/or detection of BRG1 mutation status or levels can include non-limiting examples such as analyzing and/or evaluating samples from a subject afflicted with said cancer to detect (i) nonsense or insertion/deletion (e.g., frameshift) BRG1 mutations that result in loss of protein or activity; (ii) missense BRG1 mutations that inactivate the function of the protein; (iii) changes in BRG1 gene expression levels; (iv) changes in BRG1 protein levels; and/or (v) changes in BRG1 protein function. Any of the changes, mutations, or differences are relative to a corresponding sample in another subject (e.g., a non-cancerous or normal control subject), or in the same subject at a different timepoint (e.g., after treatment with a cancer therapeutic). In parallel, for subjects afflicted with cancer exhibiting loss of BRG1 to be suitable candidates for treatment with a BRM inhibitor, the subject must retain a functional copy and/or must exhibit proper expression of the BRM gene, and subjects with dual loss of BRG1 and BRM are predicted to be insensitive to a BRM inhibitor.

Said method for analyzing, evaluating, and/or detecting BRG1 mutation status, BRG1 gene expression levels, BRG1 protein levels in parallel to BRM expression status, and/or BRG1 protein function, to predict whether a subject afflicted with cancer will respond to therapeutic treatment with a BRM inhibitor, comprises:

a) contacting a sample obtained from said afflicted subject with a reagent capable of detecting human cancer cells harboring one or more BRG1 mutations and/or one or more changes in BRG1 gene expression levels, BRG1 protein levels, and/or BRG1 protein function; and b) comparing the sample obtained from said afflicted subject with a similar sample taken from a non-cancerous or normal control subject, wherein the presence of one or more BRG1 mutations in said sample obtained from said afflicted subject indicates said afflicted subject will respond to therapeutic treatment with a BRM inhibitor, or c) comparing the sample obtained from said afflicted subject with a similar sample taken from a non-cancerous or normal control subject, wherein the expression level of BRG1 mRNA or protein in said sample obtained from said afflicted subject indicates said afflicted subject will respond to therapeutic treatment with a BRM inhibitor; and d) contacting a sample obtained from said subject with a reagent capable of detecting BRM expression levels human cancer cells.

In certain embodiments, the cancer type is any cancer type found to harbor mutations in BRG1, to show loss of BRG1 expression, to show loss or impairment of BRG1 protein fuction, and/or to show changes in BRG1 gene expression or BRG1 protein levels, while at the same time retaining a functional copy of BRM protein and/or exhibiting proper expression of BRM. Said cancer type may be described or characterized herein as "sensitive to treatment with BRM inhibitors," "sensitive to BRM therapeutic inhibition," "BRM inhibitor sensitive," or through use of similar terms.

In other embodiments, the BRM inhibitor sensitive cancer type is one associated with documented BRG1 mutations or documented loss of BRG1 expression, including cancers of the lung, breast, kidney, large intestine, ovary, prostate, upper aerodigestive tract, stomach, endometrium, liver, pancreas, haematopoietic and lymphoid tissue, skin, thyroid, pleura, autonomic ganglia, central nervous system, soft tissue, pediatric rhabdoid sarcomas, melanomas and other cancers with BRG1 loss of faction due to BRG1 mutation or loss of BRG1 expression.

In still other embodiments, the BRM inhibitor sensitive cancer is a type in which the sensitivity was experimentally observed during pooled shRNA data, as described herein. Said BRM inhibitor sensitive cancer types include lung cancer, pancreatic cancer, liver cancer, and ovarian cancer.

In certain embodiments, the reagent employed to analyze, evaluate, and/or detect BRG1 mutation status, BRG1 gene expression levels, BRG1 protein levels, and/or BRG1 protein function by methods of the invention, e.g., in human cancer cells harboring one or more BRG1 mutations, is an anti-BRG1 antibody. In certain embodiments, said reagent is one or more PCR probes, e.g., probes specific for a BRG1 mutation described herein. Saids probe can be easily designed by using techniques standard in the art to (i) sequence the BRG1 gene, or its exons, to identify mutations, e.g., such as those as listed herein; and (ii) to synthesize, or have synthesized, nucleic acid probes complementary thereto.

In certain embodiments, said probe can be designed according to sequencing and probe synthesizing techniques known in the art and used to analyze, evaluate, and/or detect a BRG1 mutation listed in Table 1, and, e.g., is a nucleic acid probe complementary to one of said mutations listed in Table 1. In certain other embodiments, said probe can be designed according to sequencing and probe synthesizing techniques known in the art and used to analyze, evaluate, and/or detect a BRG1 mutation listed in Table 2, and, e.g., is a nucleic acid probe complementary to one of said mutations listed in Table 2.

In certain embodiments, the art-recognized method of genetic sequencing and nucleic acid probe synthesis is next generation sequencing (NGS) of the BRG1 gene, exons, or mRNA using PCR probes specific to the BRG1 gene. Next generation sequencing is also referred to as high-throughput sequencing; the methods massively parallelize or scale-up the sequencing process, producing millions of sequences concurrently as distinguished from first-generation dideoxy 'Sanger' sequencing (Meldrum, C., Doyle, M. A., et al., (2011) Clin Biochem Rev. 32(4) 177-195). In certain embodiments, said reagent is one or more PCR probes, e.g., probes specific for detecting BRM mRNA levels.

In certain embodiments, the art-recognized method of genetic sequencing and nucleic acid probe synthesis is RNA sequencing of the BRG1 gene, exons, or mRNA using PCR probes specific to the transcripts of the BRG1 gene. In certain embodiments, said reagent is one or more PCR probes, e.g., probes specific for detecting BRM mRNA levels.

The above-described method of genetic sequencing and nucleic acid probe synthesis may be applied to detection of the BRM gene, exons, or mRNA as well, for instance to verify that for subjects afflicted with cancer exhibiting loss of BRG1 retain proper expression of the BRM gene.

In certain embodiments, the reagent employed to analyze, evaluate, and/or detect BRM gene expression levels, BRM protein levels, and/or BRM protein function by methods of the invention, e.g., in human cancer cells harboring one or more BRG1 mutations, is an anti-BRM antibody. In certain embodiments, said reagent is one or more PCR probes, e.g., probes specific for detecting BRM mRNA levels. In certain embodiments, the method is next generation sequencing of the BRM mRNA using PCR probes specific to the BRM gene.

Table 1 depicts a list BRG1 mutations associated with cancer cell lines and patient samples. These genetic mutations (i.e nonsense, or insertion/deletion mutations resulting in frameshifts), due to their corresponding loss of BRG1 expression, are predicted to cause loss of BRG1 function and to render cells sensitive to BRM inhibition.

Designations in the table are as follows:
fs=a frame shift mutation which produces an inactive BRG1 protein;
del=a deletion that leads to an inactive BRG1 protein;
*=a premature stop codon that leads to inactive BRG1 protein; and splice=a mutation in a splice site that leads to an inactive BRG1 protein.

The mutations listed in Table 1 are collated from literature sources, indicated in the "Reference" column, including a comprehensive list of mutations in cancer cells from the COSMIC cancer genome database (Forbes, S. A., N. Bindal, et al. (2011) Nucleic Acids Res 39 (database issue): D945-950) and the Novartis Cancer Cell Line Encycolpedia (CCLE) (Barretina, J., G. Caponigro, et al. (2012) Nature 483(7391): 603-607). The nucleic acid changes in the BRG1 gene listed in Table 1 are numbered based on their position in the BRG1 mRNA transcript for the mutations described in the COSMIC database and numbered based on their chromosomal location for the CCLE in the CCLE database. Other published annotations of BRG1 mutations in lung cancers are known from the litterature (Medina, P. P., O. A. Romero, et al. (2008) Hum Mutat 29(5): 617-622)(Imielinski, et al. (2012) Cell 150(6): 1107-1120),

TABLE 1

Summary of BRG1 mutations

| Nucleic Acid change in BRG1 Gene | Effect on BRG1 Protein (Expression or Amino Acid substitution) | Reference |
| --- | --- | --- |
| Loss of BRG1 expression | No BRG1 protein | Barretina et al. (2012) |
| c.130G>A | p.G44R | Forbes et al. (2011) |
| c.169delC | p.T58fs*36 | Forbes et al. (2011) |
| c.455delC | p.P153fs*150 | Forbes et al. (2011) |
| c.479A>G | p.Q160R | Forbes et al. (2011) |
| c.589C>T | p.P197S | Forbes et al. (2011) |
| c.729delC | p.P244fs*59 | Forbes et al. (2011) |
| c.805_806delCC | p.P270fs*16 | Forbes et al. (2011) |
| c.805delC | p.M272fs*31 | Forbes et al. (2011) |
| c.830C>A | p.P277H | Forbes et al. (2011) |
| c.991C>T | p.Q331* | Forbes et al. (2011) |
| c.1142G>A | p.R381Q | Forbes et al. (2011) |
| c.1195A>T | p.K399* | Forbes et al. (2011) |
| c.1208A>G | p.E403G | Forbes et al. (2011) |
| c.1216G>A | p.A406T | Forbes et al. (2011) |
| c.1458C>G | p.F486L | Forbes et al. (2011) |
| c.1525G>T | p.A509S | Forbes et al. (2011) |
| c.1615C>T | p.R539C | Forbes et al. (2011) |
| c.1630C>T | p.Q544* | Forbes et al. (2011) |
| c.1677_1761del85 | p.? | Forbes et al. (2011) |
| c.1733_1761+40del69 | p.? | Forbes et al. (2011) |
| c.1750A>T | p.K584* | Forbes et al. (2011) |
| c.1756A>T | p.K586* | Forbes et al. (2011) |
| c.1761G>T | p.? | Forbes et al. (2011) |
| c.1781G>C | p.G594A | Forbes et al. (2011) |
| c.1917_1918GG>CT | p.L639>? | Forbes et al. (2011) |
| c.2008G>T | p.E670* | Forbes et al. (2011) |
| c.2011G>T | p.E671* | Forbes et al. (2011) |
| c.2059A>G | p.K687E | Forbes et al. (2011) |
| c.2184_2206del23 | p.Q729fs*4 | Forbes et al. (2011) |
| c.2207A>G | p.H736R | Forbes et al. (2011) |
| c.2290T>A | p.W764R | Forbes et al. (2011) |
| c.2300C>T | p.S767F | Forbes et al. (2011) |
| c.2338G>A | p.E780K | Forbes et al. (2011) |
| c.2441C>A | p.T814K | Forbes et al. (2011) |
| c.2461G>A | p.E821K | Forbes et al. (2011) |
| c.2461G>A | p.E821K | Forbes et al. (2011) |
| c.2461G>A | p.E821K | Forbes et al. (2011) |
| c.2644G>A | p.E882K | Forbes et al. (2011) |
| c.2651A>C | p.H884P | Forbes et al. (2011) |
| c.2653C>T | p.R885C | Forbes et al. (2011) |
| c.2687T>A | p.V896E | Forbes et al. (2011) |
| c.2729C>T | p.T910M | Forbes et al. (2011) |
| c.2729C>T | p.T910M | Forbes et al. (2011) |
| c.2729C>T | p.T910M | Forbes et al. (2011) |
| c.2729C>T | p.T910M | Forbes et al. (2011) |
| c.2735C>A | p.T912K | Forbes et al. (2011) |
| c.2837C>T | p.P946L | Forbes et al. (2011) |
| c.2896C>T | p.R966W | Forbes et al. (2011) |
| c.2986A>T | p.I996F | Forbes et al. (2011) |
| c.3056C>T | p.T1019I | Forbes et al. (2011) |
| c.3146C>T | p.P1049L | Forbes et al. (2011) |
| c.3166G>T | p.E1056* | Forbes et al. (2011) |
| c.3254_3270del17 | p.L1085fs*32 | Forbes et al. (2011) |
| c.3304T>C | p.F1102L | Forbes et al. (2011) |
| c.3304T>C | p.F1102L | Forbes et al. (2011) |
| c.3306C>G | p.F1102L | Forbes et al. (2011) |
| c.3306C>G | p.F1102L | Forbes et al. (2011) |
| c.3403C>T | p.R1135W | Forbes et al. (2011) |
| c.3424T>G | p.F1142V | Forbes et al. (2011) |
| c.3469C>T | p.R1157W | Forbes et al. (2011) |
| c.3469C>T | p.R1157W | Forbes et al. (2011) |

TABLE 1-continued

Summary of BRG1 mutations

| Nucleic Acid change in BRG1 Gene | Effect on BRG1 Protein (Expression or Amino Acid substitution) | Reference |
|---|---|---|
| c.3475delG | p.L1161fs*3 | Forbes et al. (2011) |
| c.3475G>T | p.G1159W | Forbes et al. (2011) |
| c.3476delG | p.L1161fs*3 | Forbes et al. (2011) |
| c.3478G>C | p.G1160R | Forbes et al. (2011) |
| c.3488T>C | p.L1163P | Forbes et al. (2011) |
| c.3526A>T | p.S1176C | Forbes et al. (2011) |
| c.3531C>A | p.D1177E | Forbes et al. (2011) |
| c.3557C>T | p.A1186V | Forbes et al. (2011) |
| c.3566G>A | p.R1189Q | Forbes et al. (2011) |
| c.3572A>G | p.H1191R | Forbes et al. (2011) |
| c.3574C>T | p.R1192C | Forbes et al. (2011) |
| c.3694G>T | p.G1232C | Forbes et al. (2011) |
| c.3694G>A | p.G1232S | Forbes et al. (2011) |
| c.3695G>A | p.G1232D | Forbes et al. (2011) |
| c.3702C>A | p.F1234L | Forbes et al. (2011) |
| c.3706C>T | p.Q1236* | Forbes et al. (2011) |
| c.3727C>T | p.R1243W | Forbes et al. (2011) |
| c.3729_3730delGC | p.A1245fs*13 | Forbes et al. (2011) |
| c.3745G>T | p.A1249S | Forbes et al. (2011) |
| c.3850G>A | p.D1284N | Forbes et al. (2011) |
| c.3857_3858AG>CA | p.E1286A | Forbes et al. (2011) |
| c.4007G>A | p.R1336H | Forbes et al. (2011) |
| c.4271C>T | p.P1424L | Forbes et al. (2011) |
| c.4471C>T | p.R1491* | Forbes et al. (2011) |
| c.4471C>T | p.R1491* | Forbes et al. (2011) |
| c.4617C>G | p.F1539L | Forbes et al. (2011) |
| c.4698_4699GG>TT | p.K1566_E1567>N* | Forbes et al. (2011) |
| c.4801C>T | p.R1601W | Forbes et al. (2011) |
| c.4826T>C | p.L1609P | Forbes et al. (2011) |
| c.4936G>A | p.E1646K | Forbes et al. (2011) |
| g.chr19:11095992G>A | p.R89H | Barretina et al. (2012) |
| g.chr19:11097098C>T | p.P197S | Barretina et al. (2012) |
| g.chr19:11097110C>T | p.Q201* | Barretina et al. (2012) |
| g.chr19:11097617C>T | p.S266L | Barretina et al. (2012) |
| g.chr19:11097622G>A | p.V268M | Barretina et al. (2012) |
| g.chr19:11097624->C | p.V268fs | Barretina et al. (2012) |
| g.chr19:11097625CC>- | p.P269fs | Barretina et al. (2012) |
| g.chr19:11097673C>A | p.P285T | Barretina et al. (2012) |
| g.chr19:11105565C>G | p.T494R | Barretina et al. (2012) |
| g.chr19:11105573A>T | p.I497F | Barretina et al. (2012) |
| g.chr19:11105603T>C | p.Y507H | Barretina et al. (2012) |
| g.chr19:11105624G>T | p.E514* | Barretina et al. (2012) |
| g.chr19:11105651G>A | p.E523K | Barretina et al. (2012) |
| g.chr19:11106922G>A | p.D543N | Barretina et al. (2012) |
| g.chr19:11106958C>T | p.Q555* | Barretina et al. (2012) |
| g.chr19:11107056G>T | p.K587N | Barretina et al. (2012) |
| g.chr19:11113807C>- | p.L639fs | Barretina et al. (2012) |
| g.chr19:11118576A>G | p.E668_splice | Barretina et al. (2012) |
| g.chr19:11118633AGA>- | p.K689del | Barretina et al. (2012) |
| g.chr19:11118658C>G | p.D694E | Barretina et al. (2012) |
| g.chr19:11118684C>T | p.A703V | Barretina et al. (2012) |
| g.chr19:11121117GCAGTCCTACTATGCCGTGGCCC>- | p.L728fs | Barretina et al. (2012) |
| g.chr19:11121131C>T | p.A733V | Barretina et al. (2012) |
| g.chr19:11123640T>A | p.W764R | Barretina et al. (2012) |
| g.chr19:11123647T>G | p.V766G | Barretina et al. (2012) |
| g.chr19:11123672C>A | p.N774K | Barretina et al. (2012) |
| g.chr19:11123686A>G | p.D779G | Barretina et al. (2012) |
| g.chr19:11123687C>T |  | Barretina et al. (2012) |
| g.chr19:11123688G>A | p.E780K | Barretina et al. (2012) |
| g.chr19:11123701G>A | p.G784E | Barretina et al. (2012) |
| g.chr19:11123707C>T | p.T786I | Barretina et al. (2012) |
| g.chr19:11129635CGCTGTC>- | p.T814fs | Barretina et al. (2012) |
| g.chr19:11129638T>C | p.L815P | Barretina et al. (2012) |
| g.chr19:11129645C>G | p.N817K | Barretina et al. (2012) |
| g.chr19:11129655G>A | p.E821K | Barretina et al. (2012) |
| g.chr19:11129670G>T | p.A826S | Barretina et al. (2012) |
| g.chr19:11129671C>- | p.A826fs | Barretina et al. (2012) |
| g.chr19:11129735C>T |  | Barretina et al. (2012) |
| g.chr19:11130342G>A | p.E861K | Barretina et al. (2012) |
| g.chr19:11132396C>T | p.P74L | Barretina et al. (2012) |
| g.chr19:11132400G>A | p.I873_splice | Barretina et al. (2012) |
| g.chr19:11132419A>G | p.I879V | Barretina et al. (2012) |
| g.chr19:11132426A>G | p.D881G | Barretina et al. (2012) |
| g.chr19:11132437C>T | p.R885C | Barretina et al. (2012) |

TABLE 1-continued

Summary of BRG1 mutations

| Nucleic Acid change in BRG1 Gene | Effect on BRG1 Protein (Expression or Amino Acid substitution) | Reference |
| --- | --- | --- |
| g.chr19:11132438G>T | p.R885L | Barretina et al. (2012) |
| g.chr19:11132442GAA>- | p.K887del | Barretina et al. (2012) |
| g.chr19:11132457C>G | p.C891W | Barretina et al. (2012) |
| g.chr19:11132513C>T | p.T910M | Barretina et al. (2012) |
| g.chr19:11132522C>T | p.P913L | Barretina et al. (2012) |
| g.chr19:11132529G>C | p.Q915H | Barretina et al. (2012) |
| g.chr19:11132551G>C | p.A923P | Barretina et al. (2012) |
| g.chr19:11132561A>T | p.N926I | Barretina et al. (2012) |
| g.chr19:11132584A>T | p.K934* | Barretina et al. (2012) |
| g.chr19:11134230C>T | p.R966W | Barretina et al. (2012) |
| g.chr19:11134234G>A | p.R967H | Barretina et al. (2012) |
| g.chr19:11134239G>T | p.H969Y | Barretina et al. (2012) |
| g.chr19:11134251C>T | p.R973W | Barretina et al. (2012) |
| g.chr19:11134252G>A | p.R973Q | Barretina et al. (2012) |
| g.chr19:11134267G>T | p.R978L | Barretina et al. (2012) |
| g.chr19:11138497CTTGATAGAATTCTTCC>- | p.L1085fs | Barretina et al. (2012) |
| g.chr19:11138569A>G | p.M1109V | Barretina et al. (2012) |
| g.chr19:11141427G>A | p.R1135Q | Barretina et al. (2012) |
| g.chr19:11141498G>- | p.G1159fs | Barretina et al. (2012) |
| g.chr19:11141499G>T | p.G1159V | Barretina et al. (2012) |
| g.chr19:11141507G>T | p.G1162C | Barretina et al. (2012) |
| g.chr19:11141513A>T | p.N1164Y | Barretina et al. (2012) |
| g.chr19:11141547A>G | p.D1175G | Barretina et al. (2012) |
| g.chr19:11141550G>A | p.S1176N | Barretina et al. (2012) |
| g.chr19:11141556G>A | p.W1178* | Barretina et al. (2012) |
| g.chr19:11143972C>T | p.Q1185* | Barretina et al. (2012) |
| g.chr19:11143976C>T | p.A1186V | Barretina et al. (2012) |
| g.chr19:11143994G>A | p.R1192H | Barretina et al. (2012) |
| g.chr19:11144027G>A | p.R1203H | Barretina et al. (2012) |
| g.chr19:11144038G>A | p.V1207I | Barretina et al. (2012) |
| g.chr19:11144049GGA>- | p.E1212del | Barretina et al. (2012) |
| g.chr19:11144113G>A | p.G1232S | Barretina et al. (2012) |
| g.chr19:11144114G>A | p.G1232D | Barretina et al. (2012) |
| g.chr19:11144122G>T | p.D1235Y | Barretina et al. (2012) |
| g.chr19:11144148GC>- | p.R1243fs | Barretina et al. (2012) |
| g.chr19:11144150G>A | p.R1244H | Barretina et al. (2012) |
| g.chr19:11144179GAGGAGCAGGAT>- | p.EEQD1254del | Barretina et al. (2012) |
| g.chr19:11145606G>A | p.R1323H | Barretina et al. (2012) |
| g.chr19:11152007G>T | p.E1399* | Barretina et al. (2012) |
| g.chr19:11152064G>T | p.D1418Y | Barretina et al. (2012) |
| g.chr19:11152145C>T | p.R1445W | Barretina et al. (2012) |
| g.chr19:11152157C>T | p.E1449* | Barretina et al. (2012) |
| g.chr19:11152172A>C | p.N1454H | Barretina et al. (2012) |
| g.chr19:11152176C>A | p.P1455Q | Barretina et al. (2012) |
| g.chr19:11152179C>T | p.P1456L | Barretina et al. (2012) |
| g.chr19:11152215C>G | p.A1468G | Barretina et al. (2012) |
| g.chr19:11168992G>T | p.E1496* | Barretina et al. (2012) |
| g.chr19:11169001G>T | p.E1499* | Barretina et al. (2012) |
| g.chr19:11169474G>A | p.R1515H | Barretina et al. (2012) |
| g.chr19:11170474C>T | p.R1561W | Barretina et al. (2012) |
| g.chr19:11170478A>G | p.Q1562R | Barretina et al. (2012) |
| g.chr19:11170491GG>TT | p.1566_1567KE>N* | Barretina et al. (2012) |
| g.chr19:11170498G>A | p.D1569N | Barretina et al. (2012) |
| g.chr19:11170523A>G | p.E1577G | Barretina et al. (2012) |
| g.chr19:11170537G>T | p.E1582* | Barretina et al. (2012) |
| g.chr19:11170813C>T | p.R1621* | Barretina et al. (2012) |

TABLE 2

Cancer types with known BRG1 mutations shown to be sensitive to BRM shRNAs

| Cell Line | Mutation | Effect | Cancer Type |
| --- | --- | --- | --- |
| SK-HEP-1 | p.E1582* | Homozygous loss of function | liver |
| HCC-15 | M272fs/and no mRNA Expression/LOH* | Homozygous loss of function | lung |
| A549 | L728fs | Homozygous loss of function | lung |
| NCI-H1299 | T560*/ | Homozygous loss of function | lung |
| TYK-nu | No mRNA Expression/ | Homozygous loss of function | ovary |
| NCI-H838 | I873_splice | Homozygous loss of function | lung |

*LOH means "Loss of Heterozygosity," and indicates the absence of a functional tumor suppressor gene in the lost region.

In one aspect, the invention includes a method of determining the sensitivity of a cancer cell to a BRM inhibitor, comprising:

a) assaying for one or more BRG1 mutations in said cancer cell; and b) comparing the one or more BRG1 mutations with BRG1 in a non-cancerous or normal control cell, wherein the presence of said one or more BRG1 mutations in said cancer cell indicates said cell is sensitive to a BRM inhibitor.

In one aspect, the invention includes a method of determining the sensitivity of a cancer cell to a BRM inhibitor, comprising:

a) assaying for one or more BRG1 mutations in said cancer cell;

b) assaying for BRM expression in said cancer cell;

c) comparing the BRM expression with BRM expression in a non-cancerous or normal control cell; and d) comparing the one or more BRG1 mutations with BRG1 in a non-cancerous or normal control cell, wherein the presence of BRM expression, and the presence of said one or more BRG1 mutations in said cancer cell, indicates said cell is sensitive to a BRM inhibitor.

In certain embodiments, the cancer type is any cancer type found to harbor mutations in BRG1 or show loss of BRG1 expression but retain expression of BRM. In other embodiments, the cancer type is those associated documented BRG1 mutations or loss of BRG1 expression including cancer of the lung, breast, kidney, large intestine, ovary, prostate, upper aerodigestive tract, stomach, endometrium, liver, pancreas, haematopoietic and lymphoid tissue, skin, thyroid, pleura, autonomic ganglia, central nervous system, soft tissue, pediatric rhabdoid sarcomas, melanomas and other cancers with BRG1 loss of fuction due to BRG1 mutation or loss of BRG1 expression. In still other embodiments, the cancer is non-small cell lung cancer, melanoma, and ovarian cancer associated with BRG1 loss of fuction due to BRG1 mutation or loss of BRG1 expression and where we have examples In certain embodiments, the reagent employed to determine the sensitivity of a cancer cell to a BRM inhibitor is an anti-BRG1 antibody. In certain embodiments, said reagent is one or more PCR probes, e.g., probes specific for a BRG1 mutation described herein. In certain embodiments, said probe can be used to analyze, evaluate, and/or detect a BRG1 mutation listed in Table 1, e.g., is a nucleic acid probe complementary to one of said mutations listed in Table 1. In certain other embodiments, said probe can be used to analyze, evaluate, and/or detect a BRG1 mutation listed in Table 2, e.g., is a nucleic acid probe complementary to one of said mutations listed in Table 2.

In another aspect, the invention includes a method of screening for BRM inhibitors, said method comprising:

a) contacting a sample containing one or more cells harboring one or more BRG1 mutations with a candidate BRM inhibitor;

b) measuring the reduction in the growth or viability of said cells in said sample;

c) contacting a similar sample containing one or more cells harboring one or more BRG1 mutations with a known BRM inhibitor;

d) measuring the reduction in the growth or viability of said cells in said similar sample;

e) comparing the reduction in growth or viability of said cells harboring one or more BRG1 mutations from said sample with viability of said similar sample, wherein a similar reduction in viability indicates said candidate sample is a BRM inhibitor.

In another aspect, the invention includes a composition comprising a BRM inhibitor for use in treatment of cancer in a selected cancer patient population, wherein the cancer patient population is selected on the basis of its subjects harboring one or more BRG1 mutations.

In another aspect, the invention includes a kit for predicting the sensitivity of a subject afflicted with cancer for treatment with a BRM inhibitor, comprising: i) reagents capable of detecting human cancer cells harboring one or more BRG1 mutations; and ii) instructions for how to use said kit.

In the methods of the invention as described herein, methods of detecting a mutant protein or amino acid, or loss of protein expression can be performed by any method known in the art such as immunoassays, immunohistochemistry, ELISA, flow cytometry, Western blot analysis, HPLC, and mass spectrometry. In addition, in the methods of the invention as described herein, methods for detecting a mutation in a nucleic acid molecule encoding BRG1 include polymerase chain reaction (PCR), reverse transcription-polymerase chain reaction (RT-PCR), TaqMan-based assays, direct sequencing, dynamic allele-specific hybridization, high-density oligonucleotide SNP arrays, restriction fragment length polymorphism (RFLP) assays, primer extension assays, oligonucleotide ligase assays, analysis of single strand conformation polymorphism, temperaure gradient gel electrophoresis (TGGE), denaturing high performance liquid chromatography, high-resolution melting analysis, DNA mismatch-binding protein assays, SNPLex®, capillary electrophoresis, or next generation sequencing (NGS) of genomic DNA or mRNA.

BRIEF DESCRIPTION OF THE DRAWINGS

FIG. 10. Inhibition of BRM induces cell cycle arrest in BRG1-mutant NCI-H1299 tumors but not in BRG1-WT NCI-H460 tumors. a. NCI-H1299 cancer cells stably expressing dox-inducible control (CTL) nontargeting shRNA or two distinct BRM-targeting shRNAs (sh2025 or sh5537) were inoculated into mice. Tumor-bearing mice were treated for 17 days (end of study) with either vehicle or dox. Representative images of Ki67 IHC staining of NCI-H1299 tumors after 17 days of treatment are shown. b. Percentage of nuclei positive for Ki67 in NCI-H1299 tumors after 17 d of treatment. Graphs represent mean±SEM (n=8 per treatment group). c. NCI-H460 cancer cells stably expressing dox-inducible control (CTL) nontargeting shRNA or two distinct BRM-targeting shRNAs (sh2025 or sh5537) were inoculated into mice. Tumor-bearing mice were treated for 7 days or 14 days (end of study) with either vehicle or dox. Representative images of Ki67 IHC staining of NCI-H11460 tumors after 7 days (Upper panels) and 14 days (Lower panels) of treatment are shown. d. Percentage of nuclei positive for Ki67 in NCI-H460 tumors after 7 days (Left panel) or 14 days (Right panel) of treatment. Graphs represent mean±SEM (n=3 per treatment group for 7 day time point; n=8 per treatment group for 14 day time point).

DETAILED DESCRIPTION OF THE INVENTION

Epigenetic dysregulation is an emerging hallmark of cancers, and the identification of recurrent somatic mutations in chromatin modifying enzymes implies a causal role for altered chromatin states in tumorigenesis. (You, J. S. and P. A. Jones (2012) Cancer Cell 22(1): 9-20).

While the majority of epigenetic mutations are inactivating and thus do not present directly druggable targets, we reasoned that these mutations may alter the epigenomic state of cancer cells and thereby induce novel epigenetic vulnerabilities. To systematically search for epigenetic synthetic lethal interactions, we performed a pooled-shRNA screen across a large collection of cancer cell lines using a library targeting a diverse set of epigenetic regulators.

While RNAi has proven to be a very powerful forward genetic approach, the robustness and reproducibility of RNAi screens has been challenged by the prevalence of off-target effects and inability to predict high-potency shRNAs with great confidence (Sigoillot, F. D., and King, R. W., (2011 ACS Chem Biol 6(1): 47-60). In an effort to overcome these limitations, we constructed a deep coverage shRNA library which we reasoned to yield higher confidence hits clue to the extensive shRNA coverage for each gene. The shRNA library employed in this work contained 17 shRNAs per gene against a diverse collection of epigenetic regulators, with a particular focus on druggable genes, and was interrogated across a panel of 58 cell lines from the Novartis Cancer Cell Line Encyclopedia (CCLE) (Barretina, Caponigro et al. (2012) Nature 483(7391): 603-607).

The growth impact of shRNAs for each cell line was defined by a z-score (Birmingham, Ala., L. M. Selfors, et al. (2009) Nat Methods 6(8): 569-575), which is reflective of the fold change in representation of the shRNA relative to its representation in the starting plasmid pool. In addition, to take advantage of the shRNA redundancy in the deep coverage library, gene-centric p-values were calculated using the Redundant siRNA Activity (RSA) algorithm (Konig, R., C. Y. Chiang, et al. (2007) Nat Methods 4(10): 847-849).

To identify genes whose inactivation is selectively required in a subset of cancer lines, we performed k-means clustering of the RSA value for each gene (Hartigan, J. A. and Wong, M. A. (1979) Applied Statistics (28): 100-108), which defines groups of 'sensitive' and 'in-sensitive' cell lines and subsequently ranks hits based on the difference in cluster centers.

Figure 1A:
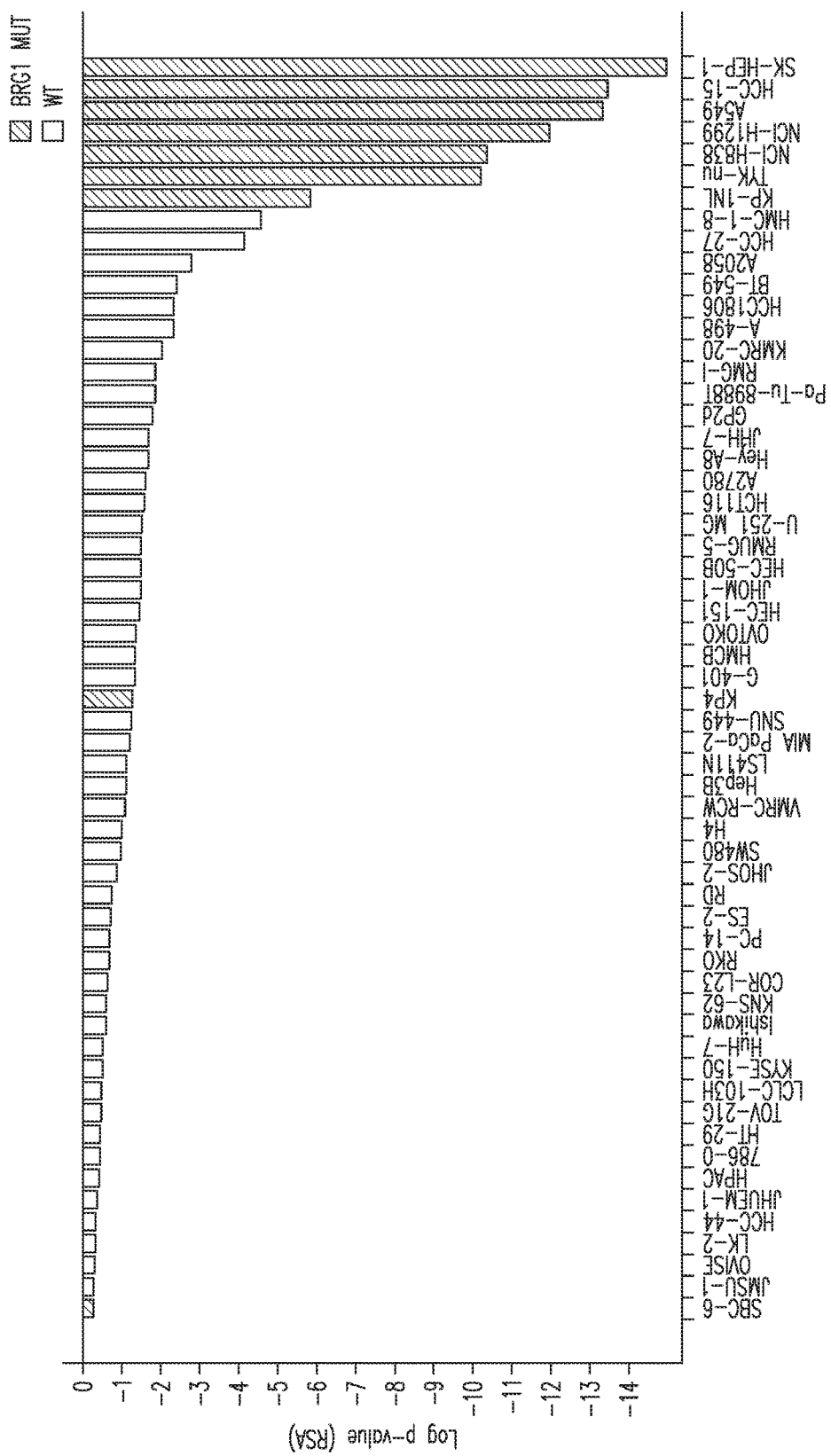
FIG. 1. An epigenome wide pooled shRNA screen identifies BRM as a synthetic lethal target in BRG1-mutant cancer cell cells. a. Waterfall plot showing the log of the p-value calculated with the RSA statistic (Konig, R., C. Y. Chiang, et al. (2007) Nat Methods 4(10): 847-849) reporting the sensitivity of each cell line in the pooled shRNA screen to knockdown of BRM. Bars colored in black are cell lines with loss of BRG1 function either due to BRG1 mutation or loss of BRG1 expression. Bars colored in grey are cell lines that are wild type (WT) for BRG1. Cell lines clustered on the right of the waterfall plot with more negative p-values are those that show growth inhibition upon BRM knockdown and all have BRG1 loss of function. b. Waterfall plots for the z-scores (Birmingham, Ala., L. M. Selfors, et al. (2009) Nat Methods 6(8): 569-575) of the 12 individual BRM shRNAs that show a statistically significant correlation in their activity profile as calculated by the ATARIS algorithm (Shao, D. D., A. Tsherniak, et al. (2013) Genome Res 23(4): 665-678), colored is as in (a). Cell lines with more negative z-scores are those that show growth inhibition upon knockdown of BRM with each individual shRNA.
Figure 1B:
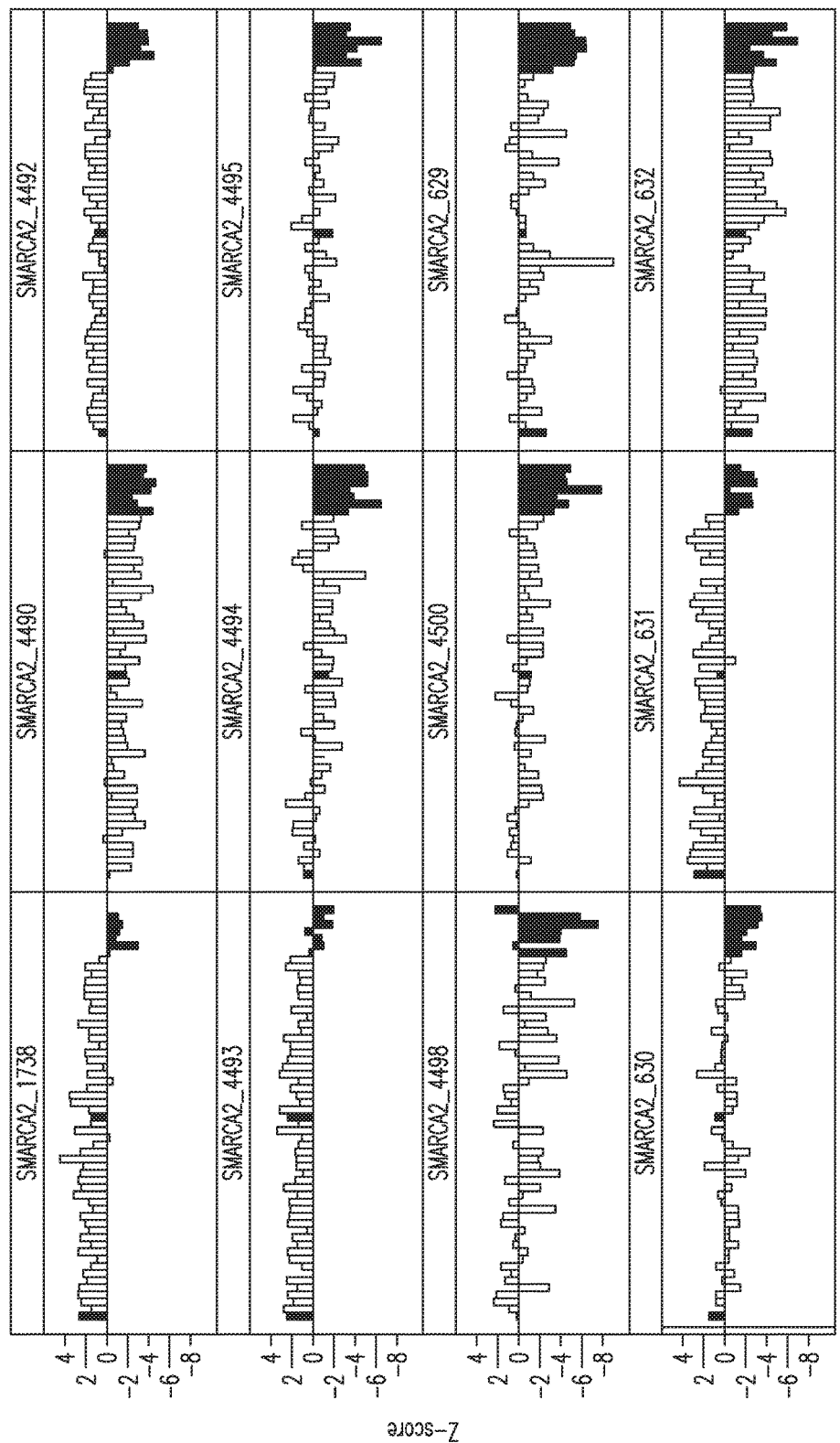

Intriguingly, the gene with the strongest robust differential lethal score from the deep coverage epigenome library screen was BRM (also known as SMARCA2), a subunit of the mSWI/SNF chromatin remodeling complexes, scoring even higher than the KRAS positive control (FIG. 1a). Application of the ATARIS algorithm (Shao, D. D., A. Tsherniak, et al. (2013) Genome Res 23(4): 665-678), which provides a statistical method for identifying shRNAs that share a common activity profile, revealed that 12 independent BRM shRNAs displayed similar lethality profiles (FIG. 1b), strongly supporting the notion that this differential lethality effect is due to knockdown of BRM rather than non-specific off-target activity. Together, these findings implicate BRM as a gene that is differentially required for the proliferation of a subset of cancer cell lines. In order to identify whether a specific genetic or molecular feature predicts sensitivity to BRM inactivation, we performed a systematic interrogation of all CCLE features, including gene expression, copy number and mutation in the CCLE data (Barretina, J., G. Caponigro, et al. (2012) Nature 483(7391): 603-607).

Strikingly, loss of function mutations in the mSWI/SNF catalytic subunit BRG1 strongly correlated with sensitivity to BRM shRNAs (p=2.03×10$^{-4}$) algorithm (Konig, R., C. Y. Chiang, et al. (2007) Nat Methods 4(10): 847-849). BRM and BRG1 are closely related paralogs that function as mutually exclusive ATPase subunits of the mSWI/SNF complexes. Even though BRM and BRG1 are significantly conserved at the protein level, they display overlapping as well as distinct functions (Ho, L. and Crabtree G. R. (2010) Nature 463(7280) 474-84). The identification of BRM as a synthetic lethal hit in the context of BRG1 mutations raised the possibility that BRM is substituting for essential functions of mSWI/SNF complexes in BRG1-deficient cancer cells, thus creating a cancer-selective vulnerability. A prediction of this model would be that only complete (i.e. homozygous) loss but not heterozygous loss of BRG1 should lead to BRM dependency. Indeed, cell lines with complete loss of BRG1 were sensitive to BRM shRNAs, whereas cells that harbored heterozygous BRG1 mutations and still retained BRG1 expression were not sensitive to BRM shRNAs (as seen in Table 2 and FIGS. 1, 2). Collectively, these findings demonstrate that cells lacking a functional copy of BRG1 become exquisitely dependent on the residual BRM containing mSWI/SNF complexes for their survival. Of note, the SBC5 cell line, which shows both loss of BRG1 and BRM expression by Western blot was not sensitive to BRM shRNAs (FIGS. 1 and 2), demonstrating that retention of BRM expression is required for BRG1 mutant cell lines to be sensitive to BRM inhibition.

Figure 3A:
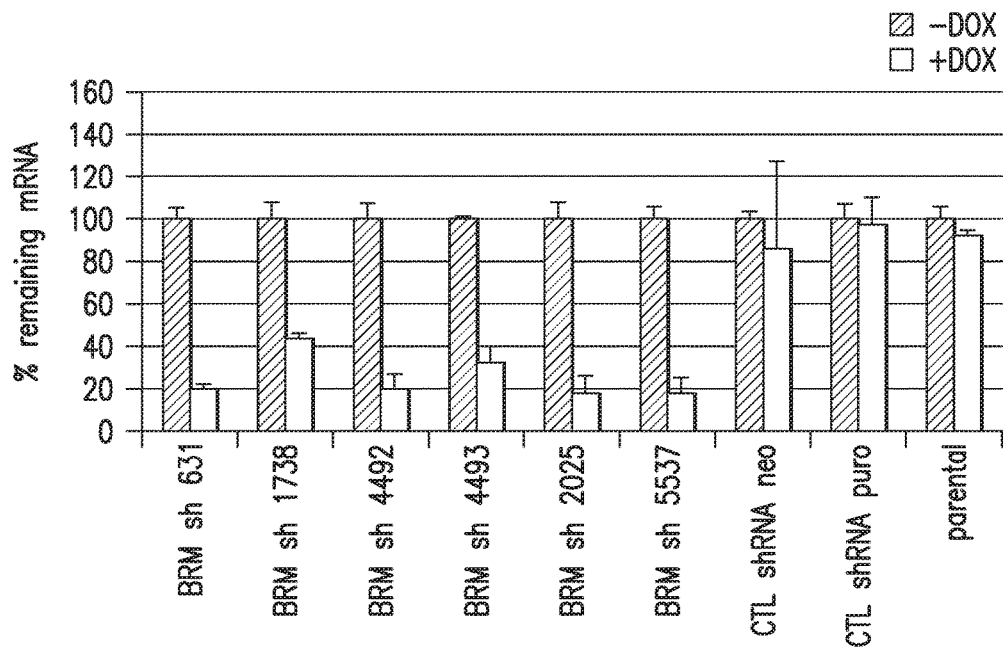
FIG. 3. BRM targeting shRNAs produce efficient BRM knockdown and do not result in off-target killing in a BRM-deficient cell line SW13. a. Quantitative Reverse Transcription (QRT-PCR) showing significant reduction of BRM mRNA transcripts in HCT116 cells upon induction of BRM shRNAs but not non-targeting control (CTL) shRNAs or parental cells with Doxycycline (Dox) (48 hours, 100 ng/mL). Values are shown as mean±standard deviation. BRM targeting shRNAs used in the pooled shRNA screening show comparable knockdown efficiency to BRM shRNAs 2025 and 5537 used in follow-up experiments. b. Induction of non-targeting control shRNAs as well as BRM shRNA 2025(c) or BRM shRNA 5537 (d) with Dox does not inhibit the growth of BRG1 and BRM-deficient SW13 cells as expected in a standard proliferation assay or (e) in a colony formation assay FIG. 4. BRM inhibition significantly and selectively inhibits the growth of BRG1-mutant cancer cells. a. Western blot showing reduction of BRM protein upon Doxycycline (Dox) treatment (120 hours, 100 ng/mL) in BRG1-mutant/deficient NCI-H838 cells stably transduced with inducible BRM shRNA-2025 or 5537. A non-targeting control (CTL) shRNA was included and did not show any decrease in BRM expression. Vinculin (VCL) was included as a loading control. b. Western blot as in (a) but in BRG1 wild type NCI-H460. Dox induction of BRM shRNAs but not CTL shRNAs results in reduction of BRM protein. β-TUBULIN was including as a loading control. c. CTL or BRM shRNA NCI-H838 cells were seeded at 500 cells per well in a 96 well plate in triplicate. Cells were treated with Dox and cell growth was measured using the cell titer glo assay at the indicated times. Dox induction of BRM shRNAs but not CTL shRNA significantly reduces cell proliferation. All assays were performed in triplicate and values are shown as mean±standard deviation d. Cell growth assay as in (d), but with CTL or BRM shRNA NCI-H460 cells. Dox induction of BRM shRNAs does not inhibit cell proliferation. All assays were performed in triplicate and values are shown as mean±standard deviation e. CTL or BRM shRNA NCI-H838 cells were seeded at 2000 cells per well. Cells were treated with Dox (100 ng/mL), and colony formation was monitored after 11 days with crystal violet staining. Dox induction of BRM shRNAs but not CTL shRNA inhibits colony formation. f. CTL or BRM shRNA NCI-H460 cells were seeded at 1000 per well, and treated with Dox and monitored for colony formation as in (e). Dox induction of BRM shRNAs, similar to CTL shRNA, does not inhibit colony formation.
Figure 3B:
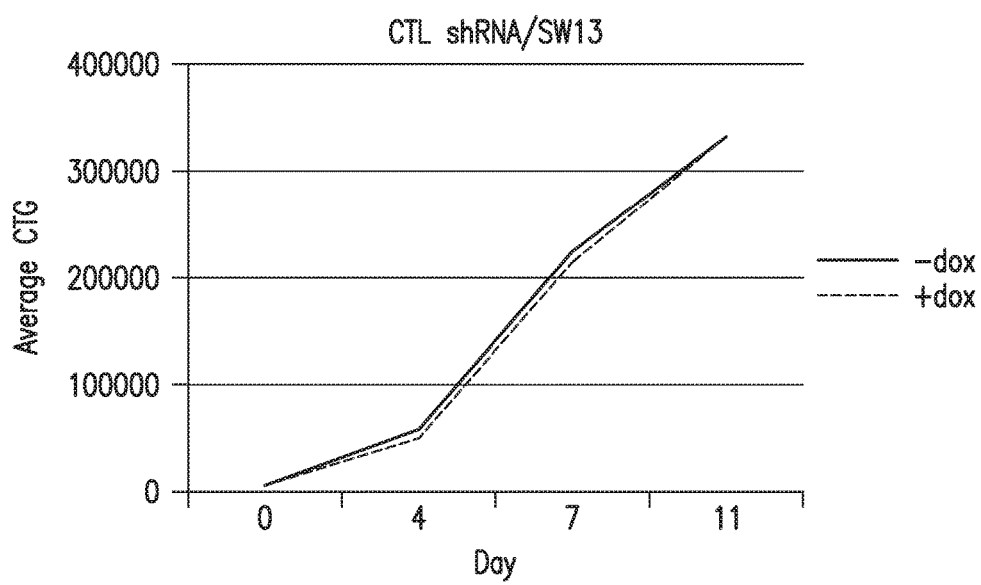
Figure 3C:
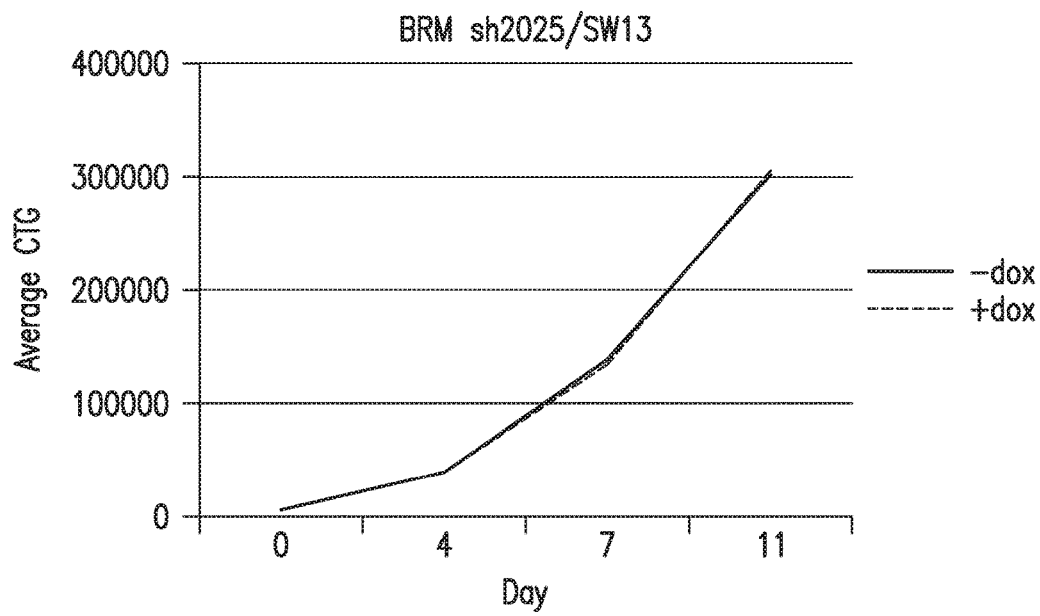
Figure 3D:
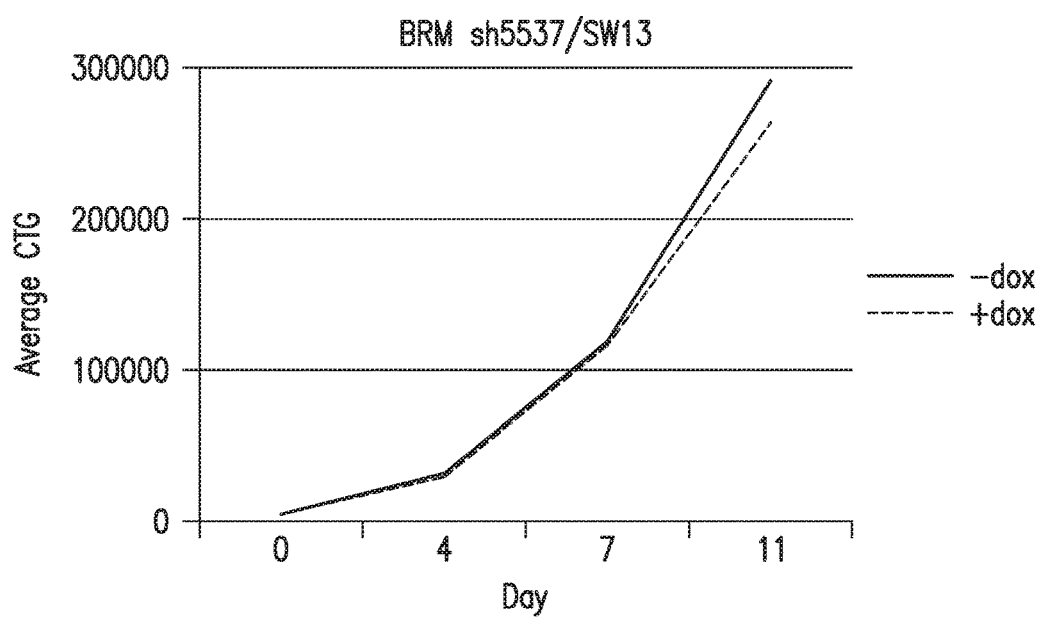
Figure 3E:
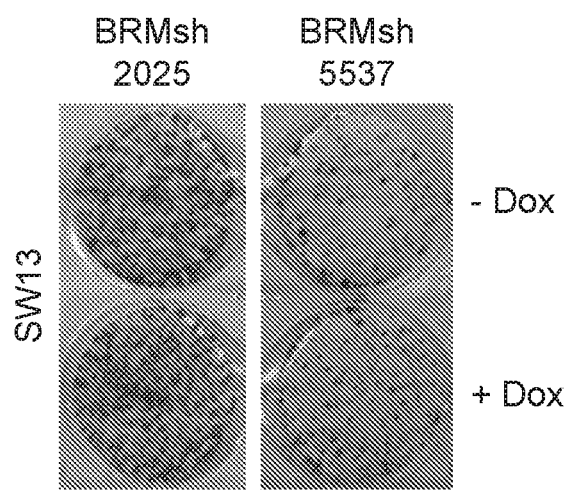

In order to further examine the impact of BRM depletion on BRG1-deficient cells, we engineered several BRG1-deficient and wild type cell lines with doxycycline (dox)-inducible shRNA constructs targeting BRM. We first verified BRM targeting shRNAs, including those sequences that were used in the pooled shRNA screening experiments resulted in efficient knockdown of BRM transcripts in a dox-inducible system (FIG. 3a). We additionally determined that the two BRM shRNAs that we applied in our subsequent validation studies (BRM shRNA 2025 and BRM shRNA 5537) did not produce any off-target growth inhibitory effects when induced in a cell line lacking the target (as seen in FIG. 3b,c,d,e).

Figure 4A:
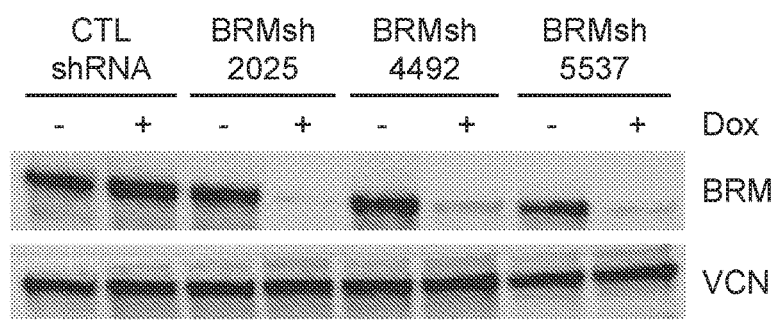
Figure 4B:
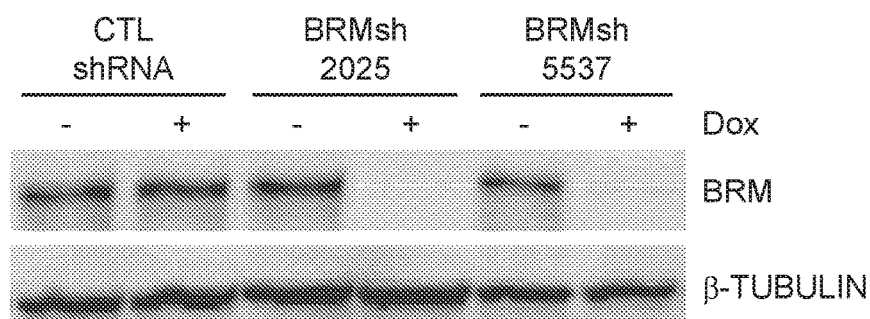
Figure 4C:
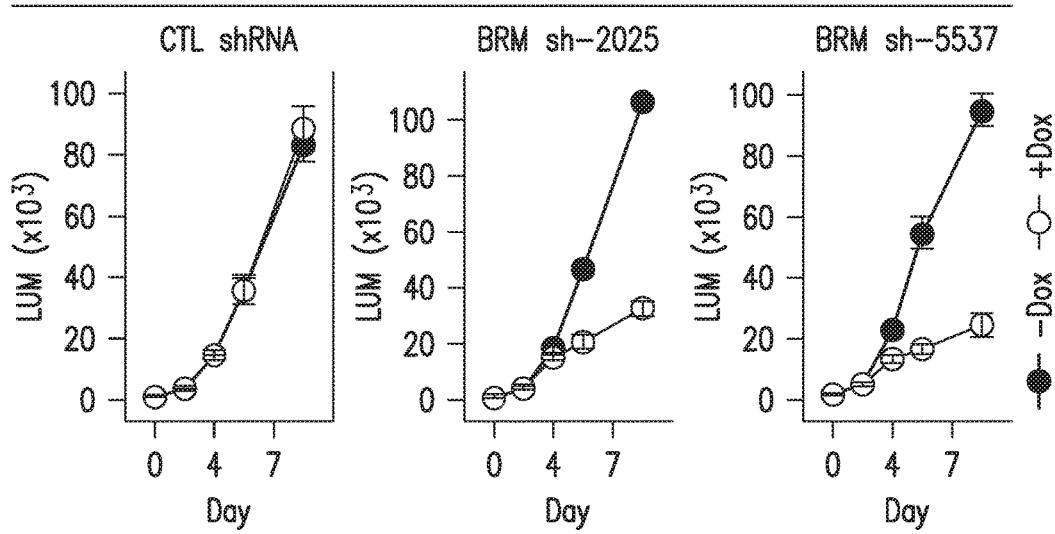
Figure 4D:
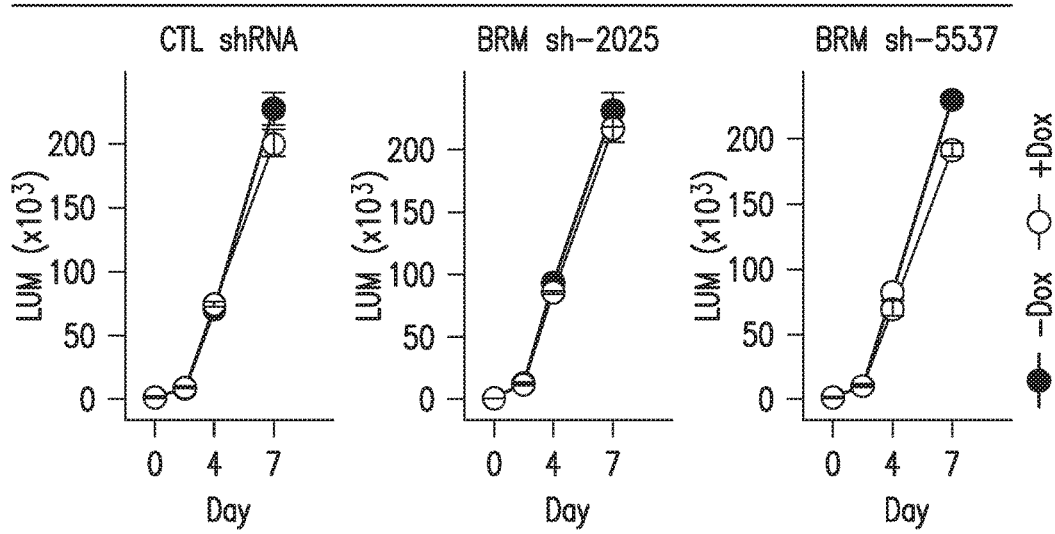
Figure 4E:
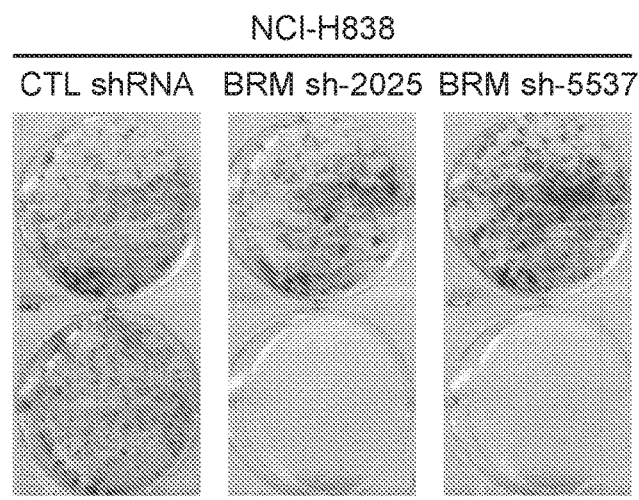
Figure 4F:
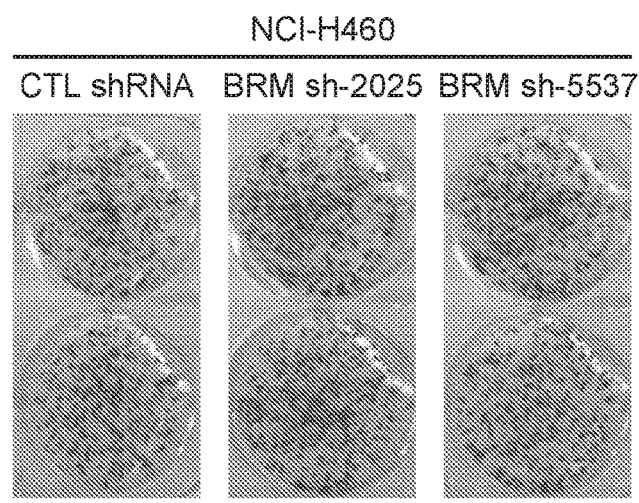
Figure 5C:
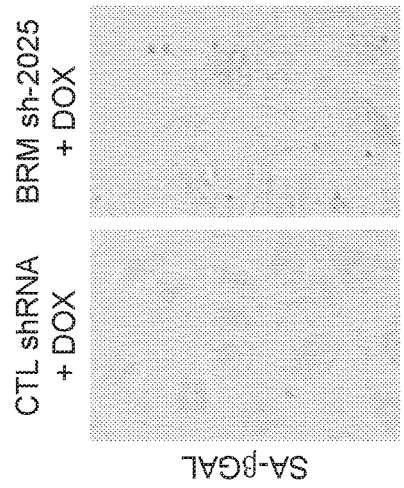
FIG. 5. BRM knockdown inhibits the growth of additional BRG1-mutant cancer cell lines. a. Western blot showing reduction of BRM protein upon Doxycycline (Dox) treatment (96 hours, 100 ng/mL) BRG1-mutant/Deficient A549 cells stably transduced with inducible BRM shRNA-2025 or 5537. A non-targeting control (CTL) shRNA was included and did not show any decrease in BRM expression. β-TUBULIN was including as a loading control. b. CTL or BRM shRNA A549 cells were seeded at 1000 cells per well in a 96 well plate in triplicate. Cells were treated with Dox and cell growth was measured using the cell titer glo assay at the indicated times. Dox induction of BRM shRNAs but not CTL shRNA significantly reduces cell proliferation. All assays were performed in triplicate and values are shown as mean±standard deviation c. Inducible BRM shRNA-2025 containing A549 cells were treated with or without Dox for 7 days, and assessed for changes in cell cycle by analysis of DNA content via Propidium Iodide staining. Percentage of cells displaying G1 and S phase content are shown on each histogram. d. CTL shRNA or BRM shRNA containing A549 cells were induced with Dox for 7 days, and monitored for senescence-associated β-galactosidase staining (blue precipitate). e. CTL or BRM shRNA A549 cells were seeded at 2000 cells per well, and treated with Dox for 13 days and monitored for colony formation with crystal violet staining. Dox induction of BRM shRNAs but not CTL shRNA inhibits colony formation. f. CTL shRNA or BRM shRNA containing A549 cells were induced with Dox for 16 days and stained for H3K9me3. g. Western blot as in (a) but in BRG1 mutant NCI-H1299 cells. h. Cell growth assay as in (b), but with CTL or BRM shRNA NCI-H1299 cells and 500 cells seeded. Dox induction of BRM shRNAs but not CTL shRNA significantly reduces cell proliferation. i. Inducible BRM shRNA-2025 containing NCI-H1299 cells were treated with or without Dox for 7 days, and assessed for changes in cell cycle by analysis of DNA content via Propidium Iodide staining. Percentage of cells displaying G1 and S phase content are shown on each histogram. j. CTL shRNA or BRM shRNA containing NCI-H1299 cells were induced with Dox for 7 days, and monitored for senescence-associated β-galactosidase staining (blue precipitate). β-galactosidase positive cells are indicated by a black arrowhead. k. CTL or BRM shRNA NCI-H1299 cells were seeded at 1000 cells per well. Cells were treated with Dox (100 ng/mL), and colony formation was monitored after 10 days with crystal violet staining. Dox induction of BRM shRNAs but not CTL shRNA inhibits colony formation. l. CTL shRNA or BRM shRNA containing NCI-H1299 cells were induced with Dox for 16 days and stained for H3K9me3.
Figure 5D:
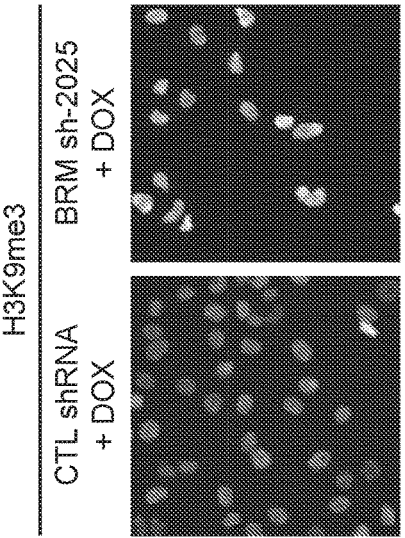
Figure 5E:
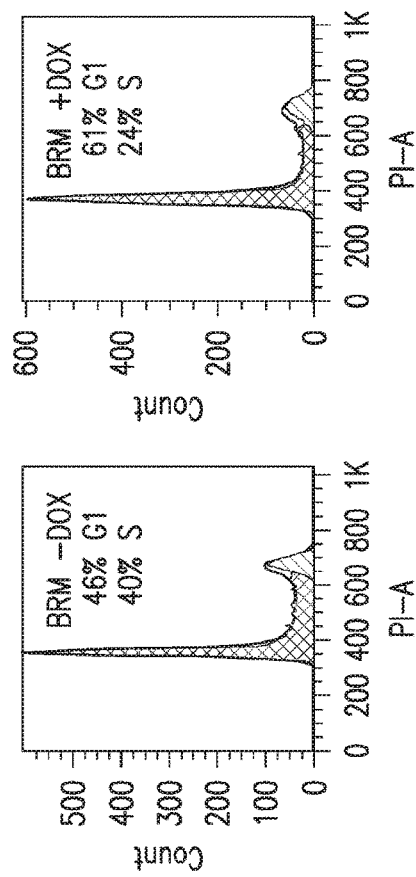
Figure 5F:
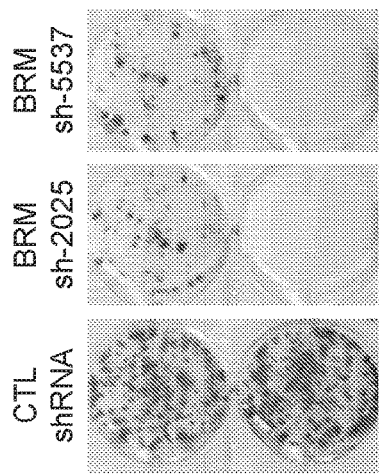
Figure 5G:
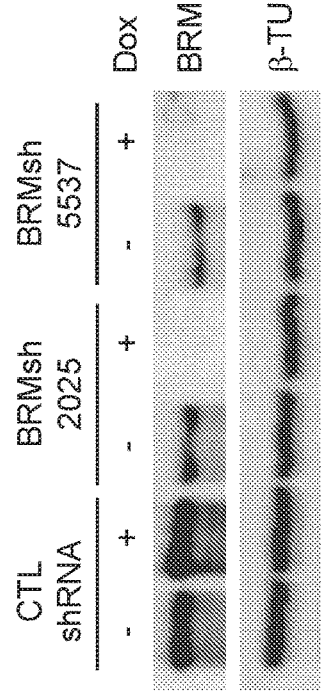
Figure 5H:
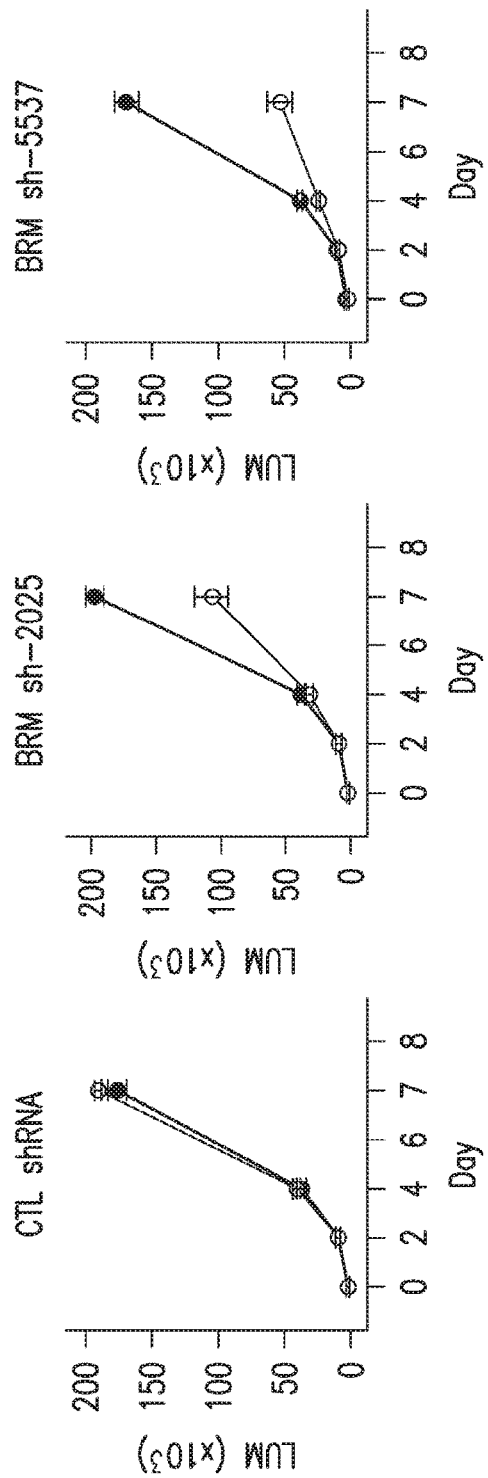
Figure 6A:
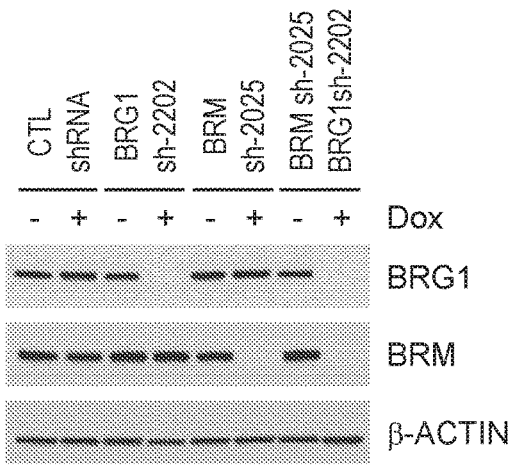
FIG. 6. Dual and not single BRG1 and BRM knockdown inhibits the growth of BRG1-WT cells. a. Western blot for BRG1 and BRM levels in lysates from CTL shRNA, BRG1 shRNA-2202, BRM shRNA-2025, or dual (BRG1 shRNA-2202 and BRM shRNA-2025) shRNA containing BEAS2B cells that were treated for 3 days with or without Dox. β-ACTIN was used as a loading control. b. CTL, BRG1 shRNA2202, BRM shRNA-2025, or dual (BRG1 shRNA-2202 and BRM shRNA-2025) shRNA containing BEAS2B cells were seeded at 500 cells per well, and treated with or without Dox for 10 days. Colony formation was monitored with crystal violet staining. c. CTL, BRG1 shRNA-2202, BRM shRNA-2025, or dual (BRG1 shRNA-2202 and BRM shRNA-2025) shRNA containing NCI-H460 cells were seeded in 6 well plates and treated for 11 or 13 days with or without Dox. Cell number was quantified by a trypan-blue exclusion assay and normalized to the Dox sample for each cell line.
Figure 6B:
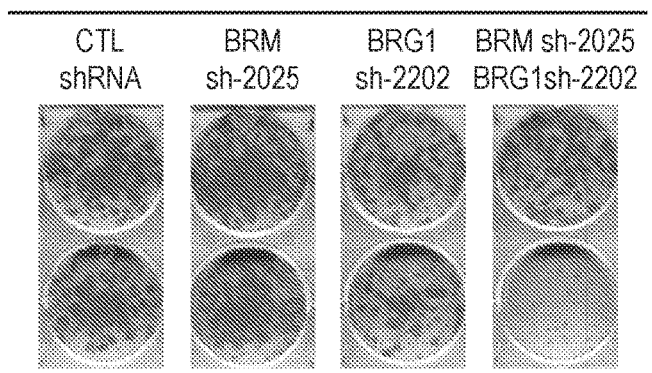
Figure 6C:
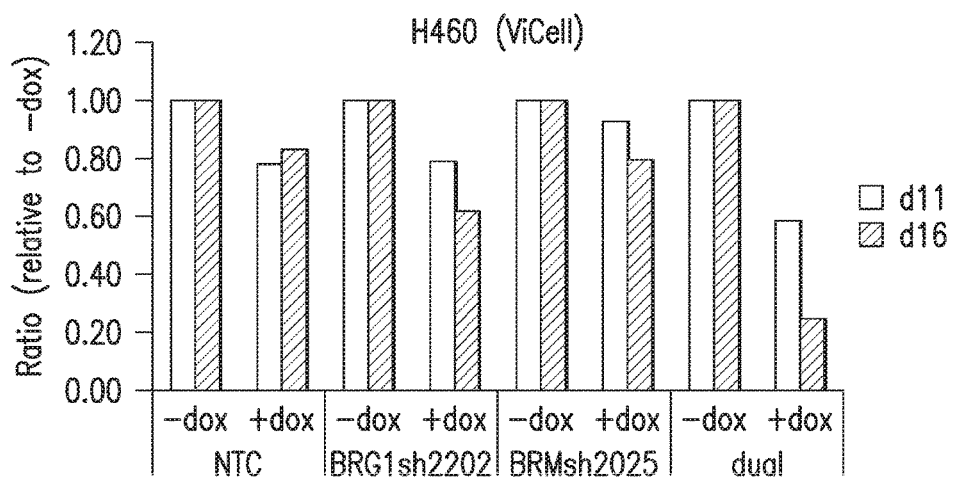

In all three BRG1-mutant lung cancer cell lines tested (NCI-H838, NCI-H1299 and A549), BRM knockdown resulted in profound growth inhibition in short-term proliferation as well as colony formation assays (as seen in FIG. 4a,c,e and FIGS. 5a,b,e,g, and k). Consistent with the results from the screening data, BRM knockdown did not affect the proliferation of cells with intact BRG1, such as the WT BRG1 lung cancer cell line NCI-H460 (as seen in FIG. 4b,d,f) and BEAS2B, a non-tumorigenic immortalized lung epithelial cell line (as seen in FIG. 6). As expected, BRG1 knockdown also did not impact the proliferation of these two BRG1 WT lines (as seen in FIG. 6). Strikingly, however, simultaneous knockdown of BRG1 and BRM led to marked growth inhibition in both of these BRG1 WT cell lines, strongly supporting the synthetic lethal relationship of BRM and BRG1 (as seen in FIG. 6).

Figure 5J:
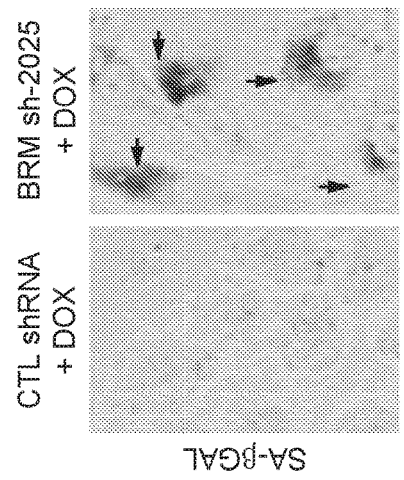
Figure 7A:
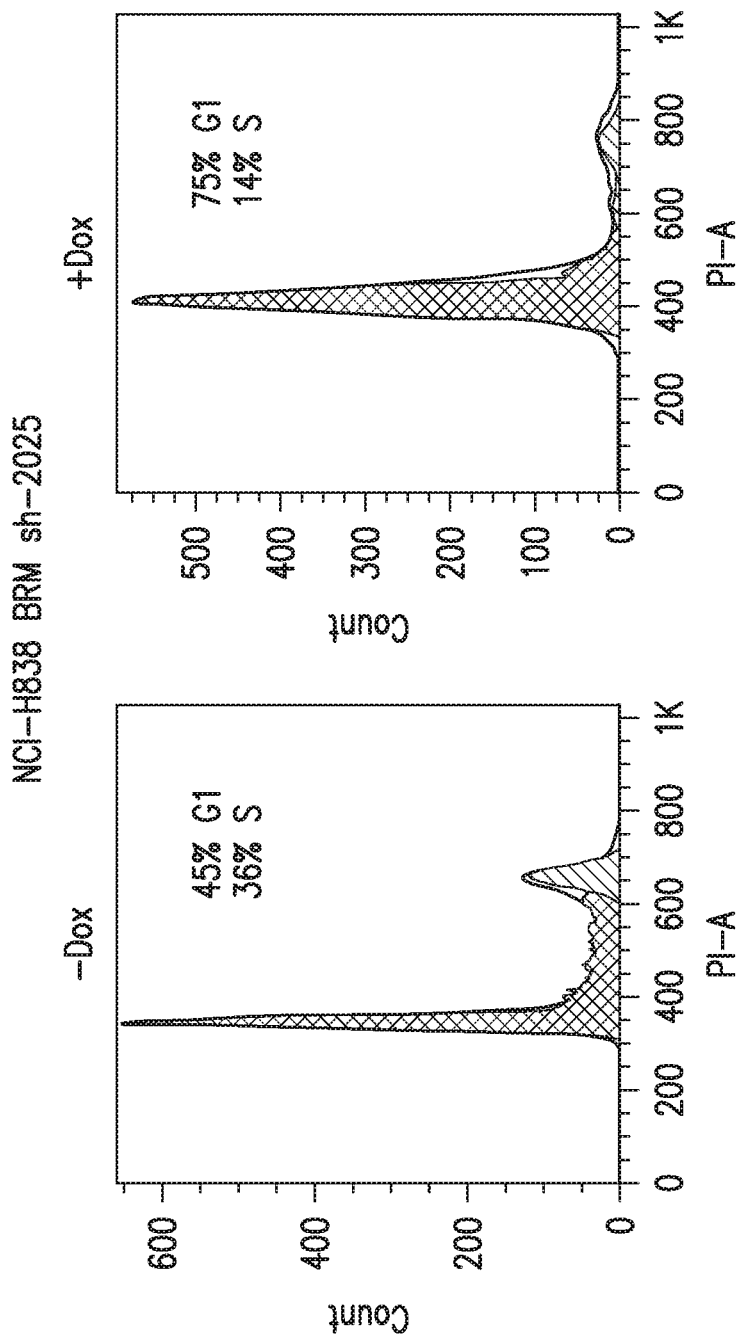
FIG. 7. BRM knockdown leads to cell cycle arrest, senescence and an increase in H3K9me3. a. BRM shRNA-2025 containing NCI-H838 cells were treated with or without Dox for 7 days, and assessed for changes in cell cycle by analysis of DNA content via Propidium Iodide staining. Percentage of cells displaying G1 and S phase content are shown on each histogram. b. CTL shRNA or BRM shRNA containing NCI-H838 cells were induced with Dox for 7 days, and monitored for senescence-associated β-galactosidase staining. β-galactosidase positive cells are indicated by a black arrowhead. c. CTL shRNA or BRM shRNA containing NCI-H838 cells were induced with Dox for 16 days and stained for H3K9me3.
Figure 7B:
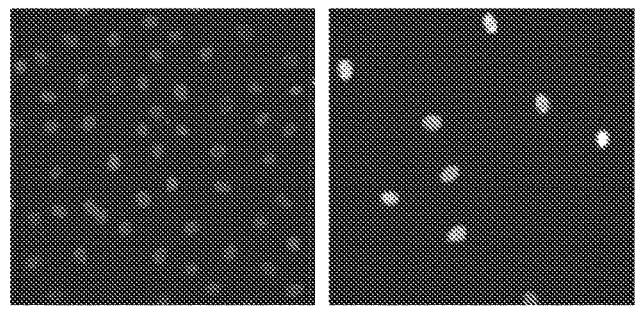

We next sought to investigate in more detail the mechanism for growth inhibition in response to BRM inactivation. Examination of cell cycle profiles in the BRG1-mutant cell lines indicated that BRM knockdown led to a prominent G1 arrest (as seen in FIG. 7a and FIG. 5c, i) without appearance of a sub-G1 population that would be otherwise indicative of cell death. Notably, in NCI-H1838 and NCI-H1299 cells, the G1 arrest was accompanied by the appearance of senescent cells as evidenced by positive staining for acidic β-galactosidase (as seen in FIG. 7b and FIG. 5j), suggesting that the growth inhibitory effect of BRM is mediated, at least in this subset of BRG1 dependent lines, through induction of G1 arrest and senescence.

Figure 5L:
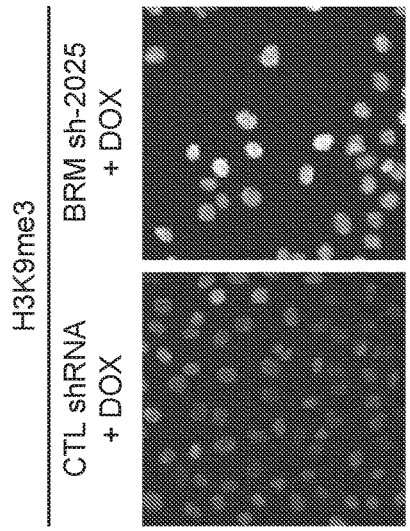
Figure 5I:
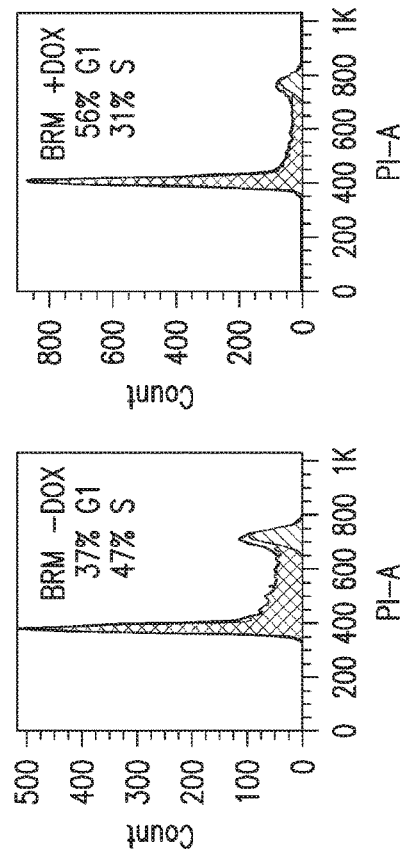
Figure 5K:
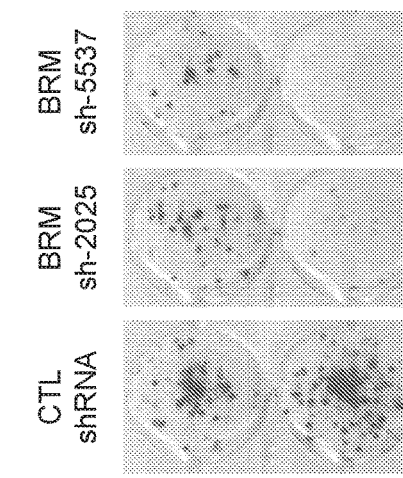
Figure 7C:
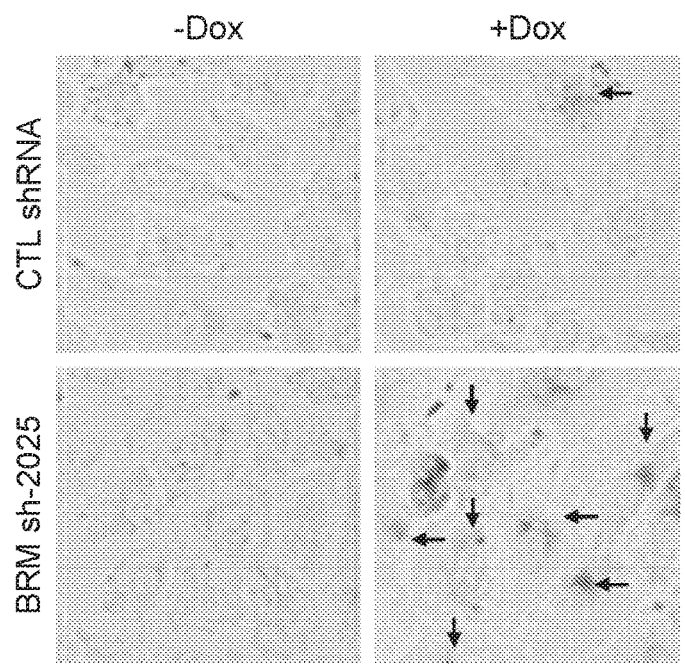

Interestingly, we observed that H3K9me3 as detected by immunofluerescenes was increased upon BRM knockdown particularly in NCI-H838 (as seen in FIG. 7c) and NCI-H1299 (as seen in FIG. 5l) cells. Of note, H3K9me3 is a repressive histone mark that is characteristic for heterochromatic gene regions and can be associated with cells undergoing senescence (Narita, M., S. Nunez, et al. (2003) Cell 113(6): 703-716). Thus, the marked increase in repressive H3K9me3 in response to BRM depletion in BRG1 mutant cells may be reflective of cells entering a growth arrested/senescent state.

In order to further understand the molecular mechanisms associated with the synthetic lethality arising from BRM inhibition in BRG1-mutant cancer cells, we carried out global transcriptional profiling studies in a time course of dox-inducible BRM knockdown in BRG1-mutant cancer cell lines, NCI-H1299 and A549. We analyzed gene expression as early as 48 hours (Day 2), as well as 72 (Day 3) and 96 hours (Day 4) following dox induction of BRM shRNAs.

The top up (greater than 1.5 fold) and down-regulated (less than −1.5 fold) genes were subsequently validated by quantitative RT-PCR and represent a diverse set of functions even though several of genes such as PLAU, GPR56, TGM2, and SPARC among others are noted to be involved in cell adhesion and extra cellular matrix (ECM) remodeling (Table 3). Of note, while many of these genes have not been previously identified and are thus novel, a subset of these genes have been reported to be modulated by BRG1 expression (Liu et al., Cell 2001, Hendricks et al., Mol Cell Biol 2004) and could thus represent common targets of BRG1 and BRM containing mSWI/SNF complexes. These results suggest that some of these genes may be direct targets of BRM (SWI/SNF), and that BRM inhibition results in transcriptional modulation of a variety of genes that re-wire the cancer cell towards growth inhibition.

Table 3 shows a list of genes verified by quantitative RT-PCR that are modulated upon BRM knockdown in NCI-H1299 and A549 cells in a time course of dox induction of BRM shRNAs. Values represent fold changes of each transcript relative to the minus dox control for each time point. Negative values represent fold decreases, and positive values represent fold increases. Fold changes from the knockdown for SMARCA2/BRM are included as controls. The taqman assay that was used to generate data for each gene is also listed. The changes in expression associated with BRM knockdown may be useful pharmacodynamics (PD) markers for monitoring the response of patients to treatment with BRM inhibitors.

could be an important means by which BRG1 loss could be determined in a patient. Upon dox treatment, BRM expression was markedly decreased in the BRM shRNA tumors but not in the CTL shRNA tumors (as seen in FIG. 8a-c and FIG. 9b-f). Efficient BRM knockdown was maintained through the end-point of the studies (as seen in FIG. 9b-f).

Figure 8G:
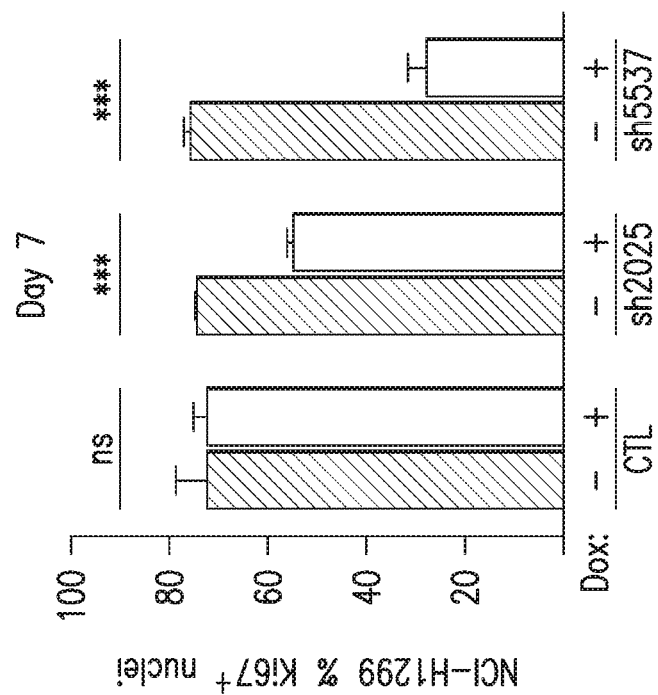
FIG. 8. BRM knockdown selectively inhibits the growth of BRG1-mutant tumors in vivo. NCI-H1299 cancer cells stably expressing dox-inducible control (CTL) nontargeting shRNA or two distinct BRM-targeting shRNAs (sh2025 or sh5537) were inoculated into mice. Tumor-bearing mice were treated for with either vehicle or dox. a. Western blot of tumor BRM and loading control VINCULIN after 7 days of treatment. b. Representative images of BRM IHC staining after 7 days of treatment. c. Percentage of nuclei positive for BRM after 7 days of treatment. Graphs represent mean±SEM (n=3 per treatment group). (d, e) NCI-H1299 d or NCI-H460 e cancer cells stably expressing dox-inducible CTL, sh2025, or sh5537 BRM shRNA were inoculated into mice. When tumor volume reached 100-300 mm$^3$, mice were treated continuously with either vehicle diet (black circles) or dox supplemented diet (white circles). The tumor volume of vehicle and dox-treated mice is plotted as the mean±SEM (n=8 per treatment group). * indicates P<0.05 of Δ tumor volume for the dox relative to vehicle-treated group. f. Representative images of Ki67 IHC staining of NCI-H1299 tumors after 7 days treatment. g. Percentage of nuclei positive for Ki67 in NCI-H1299 tumors after 7 days of treatment. Graphs represent mean±SEM (n=3 per treatment group).
Figure 8F:
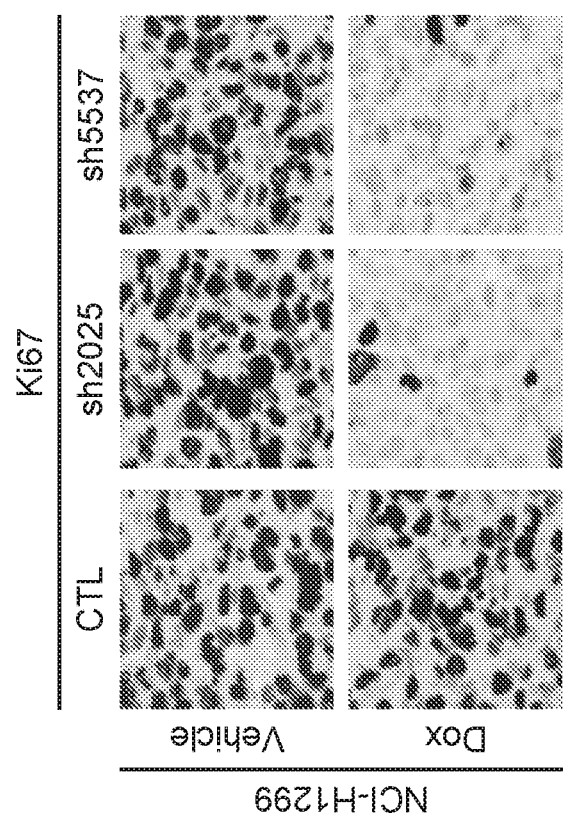

Dox treatment of mice bearing BRG1-mutant NCI-H1299 xenografts with either sh2025 or sh5537 led to significant inhibition of tumor growth (as seen in FIG. 8d). This effect was due to inhibition of BRM rather than dox treatment alone, as NCI-H1299 CTL shRNA tumors progressed rapidly despite treatment (as seen in FIG. 8d). Consistently, the proliferation marker Ki67 was significantly decreased in dox-treated NCI-H1299 BRM shRNA tumors but not in NCI-H1299 CTL shRNA tumors (as seen in FIG. 8f,g and FIG. 10a,b). In contrast, knockdown of BRM did not impact

TABLE 3

Gene expression changes following BRM knockdown

| Gene | Chromosomal Location | Entrez Gene Id | Taqman Assay ID | BRG1-Mutant NCI-H1299 Cells BRM shRNA 2025 | | | BRG1-Mutant A549 Cells BRM shRNA 2025 | | |
|---|---|---|---|---|---|---|---|---|---|
| | | | | day2 | day3 | day4 | day2 | day3 | day4 |
| SMARCA2 | chr9p22.3 | 6595 | (ABI) Hs00268234_m1 | −14.7 | −19.8 | −17.1 | −17.7 | −31.9 | −23.2 |
| GPR56 | chr16q13 | 9289 | Hs.PT.56a.40775037 | −6.7 | −11.0 | −14.0 | −3.6 | −6.5 | −8.5 |
| PLAU | chr10q24 | 5328 | Hs.PT.56a.19776078 | −5.7 | −8.5 | −9.0 | −3.5 | −12.3 | −19.0 |
| ARHGDIB | chr12p12.3 | 397 | Hs.PT.56a.20974772 | −3.3 | −7.3 | −8.5 | −3.8 | −26.5 | −41.6 |
| TGM2 | chr20q12 | 7052 | Hs.PT.56a.1937434.g | −3.4 | −3.6 | −3.3 | −4.6 | −11.7 | −11.6 |
| KRT80 | chr12q13.13 | 144501 | Hs.PT.56a.27334718.g | −4.9 | −12.5 | −29.4 | −9.4 | −42.9 | −77.9 |
| ACOX2 | chr3p14.3 | 8309 | Hs.PT.56a.38951515 | −8.3 | −0.8 | −3.4 | −3.7 | −11.6 | −12.7 |
| LINC00673 | — | 100499467 | Hs.PT.56a.27505384 | −1.6 | −1.5 | −2.0 | −1.9 | −4.7 | −7.1 |
| TGFBI | chr5q31 | 7045 | Hs.PT.56a.40848232 | −1.8 | −2.6 | −4.2 | −2.1 | −4.9 | −8.6 |
| CALB2 | chr16q22.2 | 794 | Hs.PT.56a.20381264 | −2.4 | −4.4 | −3.5 | −3.4 | −14.0 | −13.8 |
| MGLL | chr3q21.3 | 11343 | Hs.PT.56a.38969410.g | −2.9 | −5.9 | −9.8 | −2.2 | −8.6 | −18.0 |
| S100P | chr4p16 | 6286 | (ABI) Hs00195584_m1 | −1.1 | −2.5 | −1.5 | −3.1 | −17.3 | −42.5 |
| C15orf52 | chr15q15.1 | 388115 | Hs.PT.56a.4476793 | −4.0 | −5.1 | −7.6 | −4.9 | −16.3 | −26.8 |
| MYO5B | chr18q21 | 4645 | Hs.PT.56a.1129168 | −3.3 | −12.9 | −19.6 | −2.8 | −13.0 | −23.1 |
| KCNN4 | chr19q13.2 | 3783 | Hs.PT.56a.40696910.g | −2.7 | −5.1 | −9.6 | −2.0 | −6.6 | −15.1 |
| LOXL2 | chr8p21.3 | 4017 | Hs.PT.56a.2256221 | −2.1 | −2.8 | −4.1 | −2.6 | −6.8 | −12.4 |
| SPARC | chr5q31.3-q32 | 6678 | (ABI) Hs00234160_m1 | −1.7 | −4.9 | −10.6 | −6.3 | −20.0 | −34.9 |
| CLDN2 | chrXq22.3-q23 | 9075 | (ABI) Hs00252666_s1 | −4.8 | −43.0 | −158.6 | −2.4 | −5.6 | −4.7 |
| EHF | chr11p12 | 26298 | (ABI) Hs00171917_m1 | −5.3 | −192 | −32.0 | −1.4 | −2.1 | 1.1 |
| TMEM158 | chr3p21.3 | 25907 | (ABI) Hs00374916 s1 | −1.4 | −1.4 | −1.3 | −2.0 | −2.2 | −3.3 |
| MMP1 | chr11q22.3 | 4312 | (ABI) Hs00899658_m1 | −1.8 | −1.6 | −1.2 | −3.1 | −5.5 | −4.2 |
| SYP | chrXp11.23-p11.22 | 6855 | Hs.PT.56a.27207712 | 1.7 | 2.9 | 3.8 | 2.3 | 3.7 | 4.6 |
| ID4 | chr6p22-p21 | 3400 | (ABI) Hs02912975_g1 | 3.4 | 7.3 | 8.6 | 2.3 | 3.2 | 3.8 |
| ID2 | chr2p25 | 3398 | Hs.PT.56a.38958353 | 3.5 | 6.6 | 5.9 | 1.1 | 1.1 | 1.1 |
| ELFNI | chr7p22.3 | 392617 | Hs.PT.56a.14371910 | 1.4 | 1.8 | 1.7 | 2.8 | 15.8 | 16.8 |
| ADM | chr11p15.4 | 133 | Hs.PT.56a.25211580.g | 2.2 | 3.1 | 2.1 | 1.8 | 3.9 | 3.8 |
| FLJ27352 | chr15q21.3 | 145788 | Hs.PT.56a.20623801 | 1.8 | 2.9 | 2.6 | 1.5 | 2.1 | 3.2 |
| IGFBP3 | chr7p13-p12 | 3486 | Hs.PT.56a.39483881.g | 1.7 | 2.0 | 1.9 | −1.6 | −2.3 | −2.6 |
| NR4A3 | chr9q22 | 8013 | (ABI) Hs00545009_g1 | 1.9 | 2.3 | 2.0 | 5.7 | 22.3 | 38.5 |
| NR4A2 | chr2q22-q23 | 4929 | Hs.PT.56a.40037772 | 1.6 | 2.2 | 2.4 | 5.9 | 11.7 | 13.4 |
| CSPG5 | chr3p21.3 | 10675 | Hs.PT.56a.40049099 | 1.3 | 1.8 | 1.1 | 1.6 | 2.1 | 2.0 |
| PRSS35 | chr6q14.2 | 167681 | (ABI) Hs00855285_s1 | 2.1 | 6.1 | 25.7 | 1.4 | 2.3 | 2.3 |

Figure 9A:
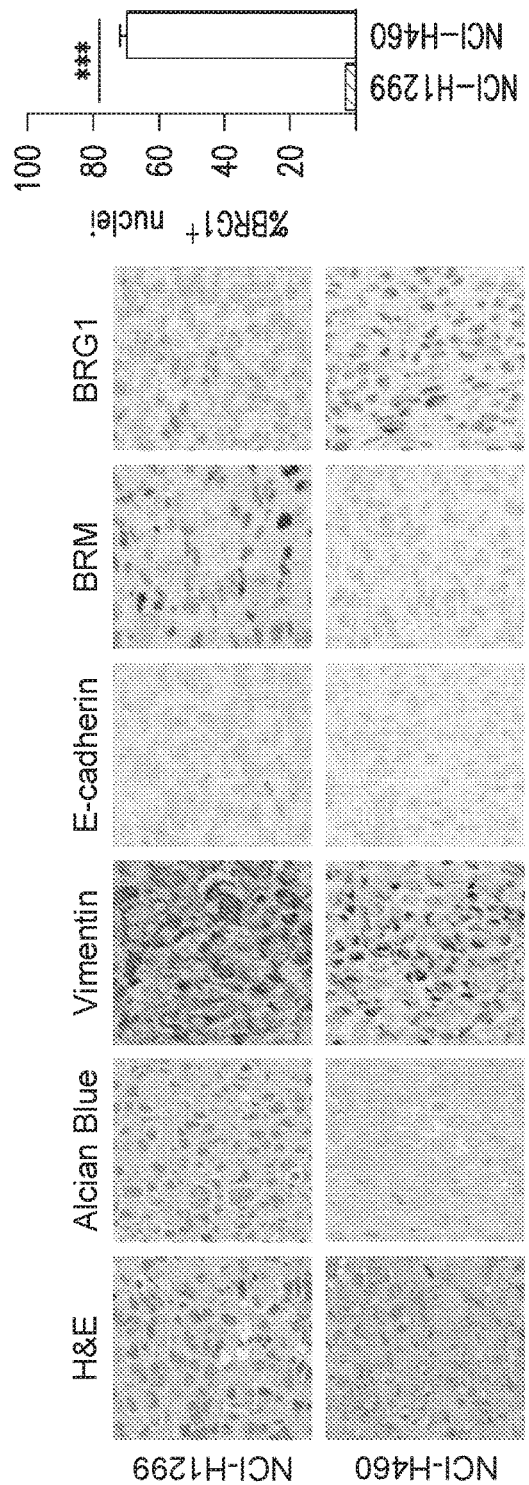
FIG. 9. Efficient and durable inhibition of BRM in NCI-H1299 and NCI-H1460 tumors in vivo. a. NCI-H1299 and NCI-H460 cancer cell lines are both derived from large cell carcinomas of the lung (Takahashi, Nau et al. 1989; Giaccone, Battey et al. 1992). Consistently, cell line xenografts of NCI-H1299 (Upper panels) and NCI-H460 (Lower panels) are composed of large, poorly differentiated tumor cells and lack mucin production. NCI-H1299 tumor cells exhibit a rhabdoid phenotype with eccentrically placed nuclei and vimentin-positive, intracytoplasmic eosinophilic inclusions. NCI-H460 tumor cells are also vimentin positive but do not show obvious intracytoplasmic eosinophilic inclusions on the H&E stain. NCI-H1299 tumor cells are BRG1 negative and show variable expression of BRM. NCI-H460 tumor cells are positive for BRG1 and show low levels of expression of BRM. Percentage of nuclei positive for BRG1 in NCI-H1299 and NCI-H460 is shown in the far right panel. Graphs represent mean±SEM (n=7-8 per treatment group). b. NCI-H1299 cancer cells stably expressing dox-inducible control (CTL) nontargeting shRNA or two distinct BRM-targeting shRNAs (sh2025 or sh5537) were inoculated into mice. Tumor-bearing mice were treated for 17 days (end of study) with either vehicle or dox. Immunoblot of tumor BRM and vinculin after 17 days of treatment shows efficient and durable BRM knockdown. c. Representative images of BRM IHC staining of NCI-H1299 tumors after 17 days of treatment. d. Percentage of nuclei positive for BRM in NCI-H1299 tumors after 17 days of treatment. Graphs represent mean±SEM (n=8 per treatment group). e. NCI-H460 cancer cells stably expressing dox-inducible control (CTL) nontargeting shRNA or two distinct BRM-targeting shRNAs (sh2025 or sh5537) were inoculated into mice. Tumor-bearing mice were treated for 7 days or 14 days (end of study) with either vehicle or dox. Due to extensive necrosis in this model, BRM IHC staining with image analysis of viable tumor regions, rather than immunoblot, proved to be the most reliable method to assess BRM knockdown efficiency. Representative images of BRM IHC staining of NCI-H460 tumors after 7 days (Upper panels) and 14 days (Lower panels) of treatment are shown. f. Percentage of nuclei positive for BRM in NCI-H460 tumors after 7 days (Left panel) or 14 days (Right panel) of treatment. Graphs represent mean±SEM (n=3 per treatment group for 7 day time point; n=7 per treatment group for 14 day time point).
Figure 9B:
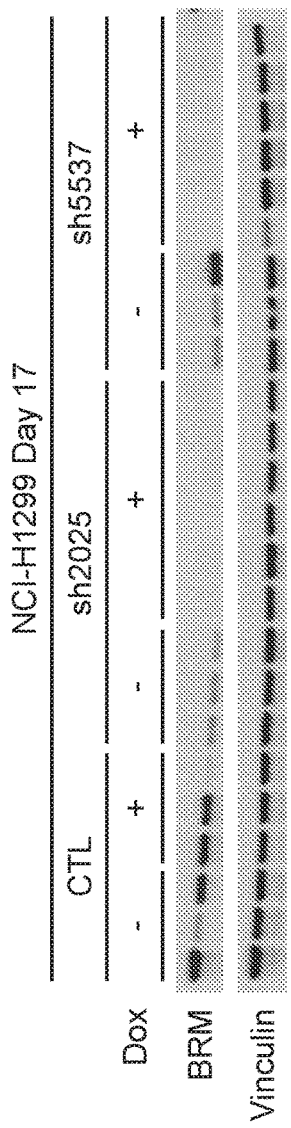

The tumor microenvironment can, in some contexts, profoundly impact the therapeutic response to chemotherapy and targeted agents. Hence, we investigated whether the selective dependency of BRG1-mutant cancers upon BRM translates into an in vivo setting. We compared the effects of BRM knockdown in BRG1-mutant NCI-H1299 and BRG1-WT NCI-H460 xenograft models (as seen in FIG. 9a), containing either dox-inducible control (CTL) non-targeting shRNA or two distinct BRM-targeting shRNAs (sh2025 or sh5537).

This data clearly shows that by immunohistochemical detection, BRG1-mutant tumors lack BRG1 expression, whereas BRG1 WT tumors retain BRG1. Therefore, this the growth of BRG1 WT NCI-H460 tumors (as seen in FIG. 8c and FIG. 10c,d), demonstrating the selective effects of BRM inhibition in vivo. Together, these findings indicate that the synthetic lethality of BRM and BRG1 translates into an in vivo setting, and lend further evidence towards the selective effects of BRM targeting.

Figure 2:
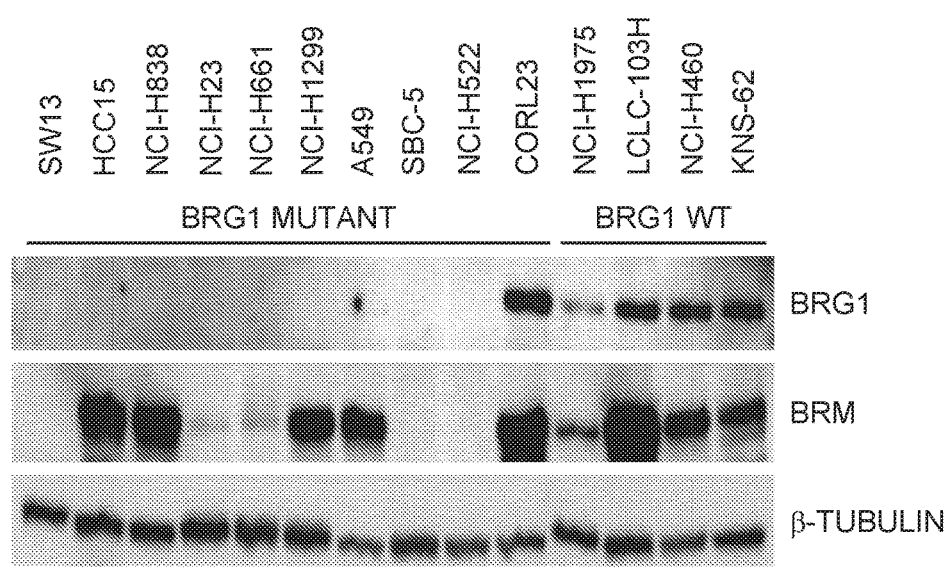
FIG. 2. Sensitivity to BRM shRNAs corresponds with loss of BRG1 protein expression. Western blot demonstrating protein levels of BRG1 and BRM in representative BRG1-mutant and wild type cancer cells lines profiled in the epigenome pooled shRNA screen. BRG1 expression is not detected in BRG1-mutant cell lines, but is present in BRG1-WT cell lines. CORL23 is a cancer cell line with a heterozygous BRG1 mutation (K689del), and thus still retains BRG1 expression. The SBC5 cell line, which shows both loss of BRG1 and BRM expression expression by Western blot was not sensitive to BRM shRNAs, as shown in FIG. 1, demonstrating that retention of BRM expression is required for BRG1-mutant cell lines to be sensitive to BRM inhibition.

The results of our study indicate that cancer cells harboring BRG1 inactivating mutations are highly sensitive to BRM inhibition, thereby demonstrating a novel role for BRM containing complexes in promoting tumor cell survival. It is interesting to note, however, that a sub-population of lung cancers with BRG1 mutations are reported to have low/no expression of BRM (Reisman, D. N., J. Sciarrotta, et al. (2003) Cancer Res 63(3): 560-566)(Matsubara, D., Y. Kishaba, et al. (2013) Cancer Sci 104(2): 266-273). While it is not known how cancer cells that lose both ATPases survive, our data indicates that BRG1-deficient cancer cells expressing BRM remain highly sensitive to BRM inhibition. In fact, we confirmed that the BRG1-deficient lines that respond to BRM shRNAs express BRM (as seen in FIG. 2). Based on the results presented in this study, we propose a model in which reduced or hypomorphic activity of the SWI/SNF complex promotes tumorigenesis. In this setting, BRG1 loss of function mutations create a cancer specific vulnerability that can be therapeutically exploited by selectively targeting this residual BRM containing complex.

Our study positions BRM as an attractive therapeutic target for BRG1-deficient cancers. Even though BRM and BRG1 are highly related, they display redundant as well as distinct roles. Whereas inactivation of BRG1 is embryonic lethal (Bultman, S., T. Gebuhr, et al. (2000) Mol Cell 6(6): 1287-1295), that of BRM results in viable animals without any overt deficiencies (Reyes, J. C., J. Barra, et al. (1998) EMBO J 17(23): 6979-6994 which predicts a good therapeutic window with BRM selective inhibitors. Of note, BRM contains a bromodomain and ATPase domain, which present attractive avenues for the development of targeted inhibitors. The clinical importance of these findings is highlighted by the prevalence of BRG1 mutations in several cancers. For example, many cancer types including lung adenocarcinomas, a subtype of lung cancer associated with poor prognosis, harbor frequent inactivating mutations in the catalytic SWI/SNF subunit BRG1/SMARCA4 (Imielinski, M., Berger, A. H., et al. (2012) Cell 150(6) 1107-20). In conclusion, our approach centered around the epigenome shRNA screen is a first set of studies to systematically elucidate a key synthetic lethal node within the SWI/SNF complex in a SWI/SNF mutant cancer, and paves the way for critical and novel avenues for therapeutic intervention in BRG1-deficient cancers.

Preparation of Samples

The invention provides, among other things, an assay for the detection of the identity of the nucleic acid sequence that encodes BRG1 mutations.

The method can include detecting the mutation in a body fluid such as blood (e.g., serum or plasma) bone marrow, cerebral spinal fluid, peritoneal/pleural fluid, lymph fluid, ascite, serous fluid, sputum, lacrimal fluid, stool, and urine, or in a tissue such as a tumor tissue. The tumor tissue can be fresh tissue or paraffin-embedded tissue.

As used herein, a "subject" refers to a human or animal, including all mammals such as primates (particularly higher primates), sheep, clog, rodents (e.g., mouse or rat), guinea pig, goat, pig, cat, rabbit, and cow. In a preferred embodiment, the subject is a human. In another embodiment, the subject is an experimental animal or animal suitable as a disease model.

Body fluid samples can be obtained from a subject using any of the methods known in the art. Methods for extracting cellular DNA from body fluid samples are well known in the art. Typically, cells are lysed with detergents. After cell lysis, proteins are removed from DNA using various proteases. DNA is then extracted with phenol, precipitated in alcohol, and dissolved in an aqueous solution. Methods for extracting acellular DNA from body fluid samples are also known in the art. Commonly, acellular DNA in a body fluid sample is separated from cells, precipitated in alcohol, and dissolved in an aqueous solution.

Generally, a solid tumor sample can be a test sample of cells or tissue that are obtained from a subject with cancer by biopsy or surgical resection. A sample of cells or tissue can be removed by needle aspiration biopsy. For this, a fine needle attached to a syringe is inserted through the skin and into the tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue can also be removed by incisional or core biopsy. For this, a cone, a cylinder, or a tiny bit of tissue is removed from the region of interest. CT imaging, ultrasound, or an endoscope is generally used to guide this type of biopsy. More particularly, the entire cancerous lesion may be removed by excisional biopsy or surgical resection. In the present invention, the test sample is typically a sample of cells removed as part of surgical resection.

The test sample of, for example tissue, may also be stored in, e.g., RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample.

Cancers amenable for treatment according to the present invention include cancers or cellular proliferative diseases such as tumors and/or cancerous cell growth associated with BRG1 mutations. Diseases may include those showing a loss of BRG1 function either through mutation in the BRG1 gene or loss of BRG1 expression. Examples of BRG1 mutations include, but are not limited to those listed in Table 1, Table 2, and experimentally described herein.

Definitions

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely exemplary and that equivalents of such are known in the art.

The terms "marker" or "biomarker" are used interchangeably herein. A biomarker is a nucleic acid or polypeptide and the presence or absence of a mutation or differential expression of the polypeptide is used to determine sensitivity to any BRM inhibitor. For example, BRG1 is a biomarker in a cancer cell when it is mutated as compared to BRG1 in normal (non-cancerous) cell or control cell.

A cell is "sensitive," displays "sensitivity" for inhibition, or is "amenable to treatment" with a BRM inhibitor when the cell viability is reduced and/or the rate of cell proliferation is reduced upon treatment with a BRM inhibitor when compared to an untreated control.

The terms "synthetic lethality," and "synthetic lethal" are used to refer to a combination of mutations in two or more genes leads to reduced cell viability and/or a reduced rate of cell proliferation, whereas a mutation in only one of these genes does not As described further herein, a cancer cell, a cancer type, or a subject afflicted with a cancer, is "BRM inhibitor sensitive," "sensitive to treatment with BRM inhibitors," "sensitive to BRM therapeutic inhibition," or described in similar terms if it is amenable to treatment with a BRM inhibitor, e.g., due to its harboring one or more BRG1 mutations of the types described herein.

"BRM" and "BRG1" refer to two paralogs of the ATPase subunit in the SWI/SNF complex, also known as SMARCA2 and SMARCA4, respectively. Unless specifically stated otherwise, BRM, as used herein, refers to human BRM, whose protein sequence has Swiss-Prot accession number P51531.2; and BRG1, as used herein, refers to human BRG1, whose protein sequence has Swiss-Prot: accession numbers P51532.2. BRM, BRG1, and the SWI/SNF complex is described in detail in such reviews as Wilson, B G, et al. Nat Rev Cancer. 2011 Jun. 9; 11(7):481-92. The BRG1 (SMARCA4) genomic sequence has NCBI Reference Sequence: NG_011556.1; its mRNAs result from a variety of splice forms (i.e., transcript variants), including NCBI Reference numbers NM_001128844.1, NM_001128849.1, NM_001128845.1, NM_001128846.1, NM_001128847.1, NM_001128848.1, and NM_003072.3. The BRM (SMARCA2) genomic sequence has NCBI Reference Sequence: NC_000009.11, it's mRNAs result from two splice forms (i.e., transcript variants), including NCBI Reference numbers NM_003070.3 and NM_139045.2.

A cancer is that is "associated with a BRG1 mutation" includes cancer types associated with documented BRG1 mutations or documented loss of BRG1 expression, including but not limited to cancers of the lung, breast, kidney, large intestine, ovary, prostate, upper aerodigestive tract, stomach, endometrium, liver, pancreas, haematopoietic and lymphoid tissue, skin, thyroid, pleura, autonomic ganglia, central nervous system, soft tissue, pediatric rhabdoid sarcomas, melanomas and other cancers with BRG1 loss of faction due to BRG1 mutation or loss of BRG1 expression.

A "wild-type," "normal," or "non-mutant" refers to sequences of BRG1 comprising accession number P51532.2.

A "mutant," or "mutation" is any change in DNA or protein sequence that deviates from wild type BRG1. This includes without limitation; single base nucleic acid changes or single amino acid changes, insertions, deletions and truncations of the wild type BRG1 gene (including all of its splice forms (i.e., transcript variants)) and its corresponding protein. Examples of BRG1 mutations can be found in Table 1, Table 2, and experimentally described herein.

A "control cell," "normal cell" or "wild-type" refers to non-cancerous tissue or cells.

A "control tissue," "normal tissue" or "wild-type" refers to non-cancerous tissue or cells.

The terms "nucleic acid" and "polynucleotide" are used interchangeably and refer to a polymeric form of nucleotides of any length, either deoxyribonucleotides or ribonucleotides or analogs thereof. Polynucleotides can have any three-dimensional structure and can perform any function. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

"Gene expression" or alternatively a "gene product" refers to the nucleic acids or amino acids (e.g., peptide or polypeptide) generated when a gene is transcribed and translated.

The term "polypeptide" is used interchangeably with the term "protein" and in its broadest sense refers to a compound of two or more subunit amino acids, amino acid analogs, or peptidomimetics. The subunits can be linked by peptide bonds. In another embodiment, the subunit may be linked by other bonds, e.g., ester, ether, etc.

As used herein the term "amino acid" refers to either natural and/or unnatural or synthetic amino acids, and both the D and L optical isomers, amino acid analogs, and peptidomimetics. A peptide of three or more amino acids is commonly called an oligopeptide if the peptide chain is short. If the peptide chain is long, the peptide is commonly called a polypeptide or a protein.

The term "isolated" means separated from constituents, cellular and otherwise, in which the polynucleotide, peptide, polypeptide, protein, antibody or fragment(s) thereof, are normally associated with in nature. For example, an isolated polynucleotide is separated from the 3' and 5' contiguous nucleotides with which it is normally associated within its native or natural environment, e.g., on the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated," "separated" or "diluted" polynucleotide, peptide, polypeptide, protein, antibody or fragment(s) thereof, is distinguishable from its naturally occurring counterpart in that the concentration or number of molecules per volume is greater in a "concentrated" version or less than in a "separated" version than that of its naturally occurring counterpart.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction"

("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in PCR: A Practical Approach, M. MacPherson et al., IRL Press at Oxford University Press (1991). All processes of producing replicate copies of a polynucleotide, such as PCR or gene cloning, are collectively referred to herein as "replication." A primer can also be used as a probe in hybridization reactions, such as Southern or Northern blot analyses (Sambrook et al., Molecular Cloning: A Laboratory Manual, 2nd edition (1989)).

As used herein, "expression" refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell.

"Differentially expressed" as applied to a gene, refers to the differential production of the mRNA transcribed and/or translated from the gene or the protein product encoded by the gene. A differentially expressed gene may be overexpressed or underexpressed as compared to the expression level of a normal or control cell. However, as used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, underexpression, is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is detected but expression in a control cell or normal tissue (e.g. non cancerous cell or tissue) is undetectable.

A high expression level of the gene can occur because of over expression of the gene or an increase in gene copy number. The gene can also be translated into increased protein levels because of deregulation or absence of a negative regulator. Lastly, high expression of the gene can occur due to increased stabilization or reduced degradation of the protein, resulting in accumulation of the protein.

A "gene expression profile" or "gene signature" refers to a pattern of expression of at least one biomarker that recurs in multiple samples and reflects a property shared by those samples, such as mutation, response to a particular treatment, or activation of a particular biological process or pathway in the cells. A gene expression profile differentiates between samples that share that common property and those that do not with better accuracy than would likely be achieved by assigning the samples to the two groups at random. A gene expression profile may be used to predict whether samples of unknown status share that common property or not. Some variation between the biomarker(s) and the typical profile is to be expected, but the overall similarity of biomarker(s) to the typical profile is such that it is statistically unlikely that the similarity would be observed by chance in samples not sharing the common property that the biomarker(s) reflects.

The term "cDNA" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

As used herein, "solid phase support" or "solid support," used interchangeably, is not limited to a specific type of support. Rather a large number of supports are available and are known to one of ordinary skill in the art. Solid phase supports include silica gels, resins, derivatized plastic films, glass beads, plastic beads, alumina gels, microarrays, and chips. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories), polyHIPE® resin (obtained from Aminotech, Canada), polyamide resin (obtained from Peninsula Laboratories), polystyrene resin grafted with polyethylene glycol (TentaGel®, Rapp Polymere, Tubingen, Germany), or polydimethylacrylamide resin (obtained from Milligen/Biosearch, Calif.).

A polynucleotide also can be attached to a solid support for use in high throughput screening assays. PCT WO 97/10365, for example, discloses the construction of high density oligonucleotide chips. See also, U.S. Pat. Nos. 5,405,783; 5,412,087 and 5,445,934. Using this method, the probes are synthesized on a derivatized glass surface to form chip arrays. Photoprotected nucleoside phosphoramidites are coupled to the glass surface, selectively deprotected by photolysis through a photolithographic mask and reacted with a second protected nucleoside phosphoramidite. The coupling/deprotection process is repeated until the desired probe is complete.

As an example, transcriptional activity can be assessed by measuring levels of messenger RNA using a gene chip such as the Affymetrix® HG-U133-Plus-2 GeneChips (Affymetrix, Santa Clara, Calif.). High-throughput, real-time quantitation of RNA of a large number of genes of interest thus becomes possible in a reproducible system.

The terms "stringent hybridization conditions" refers to conditions under which a nucleic acid probe will specifically hybridize to its target subsequence, and to no other sequences. The conditions determining the stringency of hybridization include: temperature, ionic strength, and the concentration of denaturing agents such as formamide. Varying one of these factors may influence another factor and one of skill in the art will appreciate changes in the conditions to maintain the desired level of stringency. An example of a highly stringent hybridization is: 0.015M sodium chloride, 0.0015M sodium citrate at 65-68° C. or 0.015M sodium chloride, 0.0015M sodium citrate, and 50% formamide at 42° C. An example of a "moderately stringent" hybridization is the conditions of: 0.015M sodium chloride, 0.0015M sodium citrate at 50-65° C. or 0.015M sodium chloride, 0.0015M sodium citrate, and 20% formamide at 37-50° C. The moderately stringent conditions are used when a moderate amount of nucleic acid mismatch is desired. One of skill in the art will appreciate that washing is part of the hybridization conditions. For example, washing conditions can include 02.x-0.1×SSC/0.1% SDS and temperatures from 42-68° C., wherein increasing temperature increases the stringency of the wash conditions.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology, Ausubel et al., eds., (1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant.

The term "cell proliferative disorders" shall include dysregulation of normal physiological function characterized by abnormal cell growth and/or division or loss of function. Examples of "cell proliferative disorders" includes but is not limited to hyperplasia, neoplasia, metaplasia, and various autoimmune disorders, e.g., those characterized by the dysregulation of T cell apoptosis.

As used herein, the terms "neoplastic cells," "neoplastic disease," "neoplasia," "tumor," "tumor cells," "cancer," and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A "metastatic cell or tissue" means that the cell can invade and destroy neighboring body structures. Cancer can include without limitation, diffuse Large B cell lymphoma, lymphoma, lymphocytic leukemia, acute lymphoblastic B cell leukemia and Burkitts lymphoma.

The term "PBMC" refers to peripheral blood mononuclear cells and includes "PBL"—peripheral blood lymphocytes.

"Suppressing" or "suppression" of tumor growth indicates a reduction in tumor cell growth when contacted with a BRM inhibitor compared to tumor growth without contact with a BRM inhibitor compound. Tumor cell growth can be assessed by any means known in the art, including, but not limited to, measuring tumor size, determining whether tumor cells are proliferating using a 3H-thymidine incorporation assay, measuring glucose uptake by FDG-PET (fluorodeoxyglucose positron emission tomography) imaging, or counting tumor cells. "Suppressing" tumor cell growth means any or all of the following states: slowing, delaying and stopping tumor growth, as well as tumor shrinkage.

A "subject," "individual" or "patient" is used interchangeably herein, which refers to a vertebrate, preferably a mammal, more preferably a human. Mammals include, but are not limited to, mice, simians, humans, farm animals, sport animals, and pets.

Detection of BRG1 Mutations

The detection of BRG1 mutations can be clone by any number of ways, for example: DNA sequencing, PCR based methods, including RT-PCR, microarray analysis, Southern blotting, Northern blotting, Next Generation Sequencing, and dip stick analysis.

The polymerase chain reaction (PCR) can be used to amplify and identify BRG1 mutations from either genomic DNA or RNA extracted from tumor tissue. PCR is well known in the art and is described in detail in Saiki et al., Science 1988, 239:487 and in U.S. Pat. No. 4,683,195 and U.S. Pat. No. 4,683,203.

Methods of detecting BRG1 mutations by hybridization are provided. The method comprises identifying a BRG1 mutation in a sample by contacting nucleic acid from the sample with a nucleic acid probe that is capable of hybridizing to nucleic acid with a BRG1 mutation or fragment thereof and detecting the hybridization. The nucleic acid probe is detectably labeled with a label such as a radioisotope, a fluorescent agent or a chromogenic agent. Radioisotopes can include without limitation; 3H, 32P, 33P and 35S etc. Fluorescent agents can include without limitation: FITC, texas red, rhodamine, etc.

The probe used in detection that is capable of hybridizing to nucleic acid with a BRG1 mutation can be from about 8 nucleotides to about 100 nucleotides, from about 10 nucleotides to about 75 nucleotides, from about 15 nucleotides to about 50 nucleotides, or about 20 to about 30 nucleotides. The probe or probes can be provided in a kit, which comprise at least one oligonucleotide probe that hybridizes to or hybridizes adjacent to a BRG1 mutation. The kit can also provide instructions for analysis of patient cancer samples that can contain a BRG1 mutation, and which BRG1 mutations indicate that the patient is sensitive or insensitive to treatment with a BRM inhibitor.

Single stranded conformational polymorphism (SSCP) can also be used to detect BRG1 mutations. This technique is well described in Orita et al., PNAS 1989, 86:2766-2770.

Antibodies directed against BRG1 can be useful in the detection of cancer and the detection of mutated forms of BRG1. Antibodies can be generated which recognize and specifically bind only a specific mutant of BRG1 and do not bind (or weakly bind) to wild type BRG1. These antibodies would be useful in determining which specific mutation was present and also in quantifying the level of BRG1 protein. For example, an antibody can be directed against a functional domain of a BRG1 protein, such as the ATPase domain or bromodomain. An antibody that recognizes this amino acid change and does not specifically bind to wild type BRG1 could identify the specific mutation in tissue sections and also the protein levels by Western blotting. Such antibodies can be generated against a BRG1 mutation by using peptides containing the specific BRG1 mutation of interest.

A cancer cell believed to contain a BRG1 mutation can be lysed and Western blotting performed to detect the amount of BRG1 mutant protein, using a cell containing wild type BRG1 as a control.

Antibodies directed against BRM can be useful in the detection of the expression level of BRM. Similarly, a cancer cell believed to contain a BRG1 mutation can be lysed and Western blotting performed to detect the level of BRM protein using and compared to a sample with known BRM expression as a control.

Measurement of Gene Expression

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

In one aspect, gene expression is detected and quantitated by hybridization to a probe that specifically hybridizes to the appropriate probe for that biomarker. The probes also can be attached to a solid support for use in high throughput screening assays using methods known in the art. WO 97/10365 and U.S. Pat. Nos. 5,405,783, 5,412,087 and 5,445,934, for example, disclose the construction of high density oligonucleotide chips which can contain one or more of the sequences disclosed herein. Using the methods disclosed in U.S. Pat. Nos. 5,405,783, 5,412,087 and 5,445, 934, the probes of this invention are synthesized on a derivatized glass surface. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

In one aspect, the expression level of a gene is determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device. See U.S. Pat. Nos. 5,578,832 and 5,631,734.

Alternatively any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, Mg 2+ and or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present disclosure include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the coloured label.

The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Detection of Polypeptides

BRG1 mutations when translated into proteins can be detected by specific antibodies. Mutations in the BRG1 protein can change the antigenicity of the BRG1 protein, so that an antibody raised against a BRG1 mutant antigen (e.g. a specific peptide containing a mutation) will specifically bind the mutant BRG1 and not recognize the wild-type.

Expression level of BRG1 mutations can also be determined by examining protein expression or the protein product of BRG1 mutants. Determining the protein level involves measuring the amount of any immunospecific binding that occurs between an antibody that selectively recognizes and binds to the polypeptide of the biomarker in a sample obtained from a patient and comparing this to the amount of immunospecific binding of at least one biomarker in a control sample. The amount of protein expression of the BRG1 can be increased or reduced when compared with control expression.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), Western blot analysis, immunoprecipitation assays, immunofluorescent assays, flow cytometry, immunohistochemistry, HPLC, mass spectrometry, confocal microscopy, enzymatic assays, surface plasmon resonance and PAGE-SDS.

Assaying for Biomarkers and BRM Inhibitor Treatment

Once a patient has been assayed for BRG1 status and predicted to be sensitive to treatment with a BRM inhibitor, administration of any BRM inhibitor to a patient can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the close level and pattern being selected by the treating physician. Suitable dosage formulations and methods of administering the agents may be empirically adjusted.

BRG1 mutations can be assayed for after BRM inhibitor administration in order to determine if the patient remains sensitive to the BRM inhibitor treatment. In addition, BRG1 mutations can be assayed for in multiple timepoints after a single administration of a BRM inhibitor. For example, after an initial bolus of an BRM inhibitor is administered, a BRG1 mutation can be assayed for at 1 hour, 2 hours, 3 hours, 4 hours, 8 hours, 16 hours, 24 hours, 48 hours, 3 clays, 1 week or 1 month or several months after the first treatment.

BRG1 mutations can be assayed for after each BRM inhibitor administration, so if there are multiple BRM inhibitor administrations, then assaying for BRG1 mutations for after each administration can determine continued patient sensitivity. The patient could undergo multiple BRM inhibitor administrations and then assayed for BRG1 mutations at different timepoints. For example, a course of treatment may require administration of an initial dose of BRM inhibitor, a second dose a specified time period later, and still a third dose hours after the second dose. BRG1 mutations can be assayed for at 1 hour, 2 hours, 3 hours, 4 hours, 8 hours, 16 hours, 24 hours, 48 hours, 3 days, 1 week or 1 month or several months after administration of each dose of a BRM inhibitor.

Finally, different BRM inhibitors can be administered and followed by assaying for a BRG1 mutation. In this embodiment, more than one BRM inhibitor is chosen and administered to the patient. BRG1 mutation can then be assayed for after administration of each different BRM inhibitor. This assay can also be done at multiple timepoints after administration of the different BRM inhibitor. For example, a first BRM inhibitor could be administered to the patient and BRG1 mutation assayed for at 1 hour, 2 hours, 3 hours, 4 hours, 8 hours, 16 hours, 24 hours, 48 hours, 3 days, 1 week or 1 month or several months after administration. A second BRM inhibitor could then be administered and BRG1 mutation can be assayed for again at 1 hour, 2 hours, 3 hours, 4 hours, 8 hours, 16 hours, 24 hours, 48 hours, 3 days, 1 week or 1 month or several months after administration of the second BRM inhibitor.

Kits for assessing the activity of any BRM inhibitor can be made. For example, a kit comprising nucleic acid primers for PCR or for microarray hybridization for a BRG1 mutation can be used for assessing BRM inhibitor sensitivity (i.e., amenability to treatment with one or more BRM inhibitors). Alternatively, a kit supplied with antibodies for the BRG1 mutations listed in Table 2 would be useful in assaying for BRM inhibitor sensitivity.

It is well known in the art that cancers can become resistant to chemotherapeutic treatment, especially when that treatment is prolonged. Assaying for a BRG1 mutation can be clone after prolonged treatment with any chemotherapeutic to determine if the cancer would be sensitive to the BRM inhibitor. If the patient has been previously treated with another chemotherapeutic or another BRM inhibitor, it is useful to assay for a BRG1 mutation to determine if the tumor is sensitive to a BRM inhibitor. This assay can be especially beneficial to the patient if the cancer goes into remission and then re-grows or has metastasized to a different site.

Screening for BRM Inhibitors

It is possible to use BRG1 mutations to screen for BRM inhibitors. This method comprises providing for a cell containing a BRG1 mutation from Table 1 or with loss of BRG1 expression, contacting the cell with a candidate BRM inhibitor and the IC50 of the treated cell is compared with a known BRM inhibitor contacting a cell that is wild type for BRG1.

The BRG1 mutations described herein can be detected by any known method in the art. For example, a BRG1 mutation referred to herein is to the sense strand of the gene for convenience. As recognized by the skilled artisan, however, nucleic acid molecules containing the gene may be complementary double stranded molecules and thus reference to a particular site on the sense strand refers as well to the corresponding site on the complementary antisense strand. That is, reference may be made to the same mutant site on either strand and an oligonucleotide may be designed to hybridize specifically to either strand at a target region containing the polymorphic and/or mutant site. Thus, the invention also includes single-stranded polynucleotides and mutations that are complementary to the sense strand of the genomic variants described herein.

Many different techniques can be used to identify if the nucleic acid sequence encodes a BRG1 mutation, including single-strand conformation polymorphism (SSCP) analysis, heteroduplex analysis by denaturing high-performance liquid chromatography (DHPLC), direct DNA sequencing and computational methods (Shi et al, Clin Chem A1U6AA12 (2001)). The most common methods currently include hybridization, primer extension, and cleavage methods. Each of these methods must be connected to an appropriate detection system. Detection technologies include fluorescent polarization (Chan et al., Genome Res. 9:492-499 (1999)), luminometric detection of pyrophosphate release (pyrosequencing) (Ahmadiian et al., Anal. Biochem. 280:103-10 (2000)), fluorescence resonance energy transfer (FRET)-based cleavage assays, DHPLC, and mass spectrometry (Shi, Clin Chem 47:164-172 (2001); U.S. Pat. No. 6,300,076 B1). In one embodiments, an automatic analyzer (e.g., a PCR machine or an automatic sequencing machine) can be used to determine the presence or absence of a BRG1 mutation. All such methods are well known by skilled artisans.

In a particularly preferred embodiment, mutations can be detected using INVADER™ technology (available from Third Wave Technologies Inc. Madison, Wis. USA). In this assay, a specific upstream "invader" oligonucleotide and a partially overlapping downstream probe together form a specific structure when bound to complementary DNA template. This structure is recognized and cut at a specific site by the Cleavase enzyme, resulting in the release of the 5' flap of the probe oligonucleotide. This fragment then serves as the "invader" oligonucleotide with respect to synthetic secondary targets and secondary fluorescently labelled signal probes contained in the reaction mixture. This results in specific cleavage of the secondary signal probes by the Cleavase enzyme. Fluorescent signal is generated when this secondary probe (labelled with dye molecules capable of fluorescence resonance energy transfer) is cleaved. Cleavases have stringent requirements relative to the structure formed by the overlapping DNA sequences or flaps and can, therefore, be used to specifically detect single base pair mismatches immediately upstream of the cleavage site on the downstream DNA strand. Ryan D et al., Molecular Diagnosis 4(2): 135-144 (1999) and Lyamichev V et al. Nature Biotechnology 17: 292-296 (1999), see also U.S. Pat. Nos. 5,846,717 and 6,001,567.

The invention further includes compositions which contain oligonucleotide probes and primers designed to specifically hybridize to the nucleic acid sequence that encodes a BRG1 mutation, or that are adjacent to a mutant site. The region containing the mutation of interest can be amplified using any oligonucleotide-directed amplification method, including but not limited to polymerase chain reaction (PCR). (U.S. Pat. No. 4,965,188), ligase chain reaction (LCR) (Barany et al, Proc. Natl. Acad. ScL USA 88:189-193 (1991); published PCT patent application WO 90/01069), and oligonucleotide ligation assay (OLA) (Landegren et al, Science 241: 1077-1080 (1988)). Oligonucleotides useful as primers or probes in such methods should specifically hybridize to a region of the nucleic acid that contains or is adjacent to the polymorphic/mutant site. Typically, the oligonucleotides, are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the region containing the BRG1 mutation includes transcription-based amplification systems (U.S. Pat. No. 5,130,238; EP 329,822; U.S. Pat. No. 5,169,766, published PCT patent application WO 89/06700) and isothermal methods. (Walker et al., Proc. Natl. Acad. Sci. USA 89: 392-396 (1992)).

A mutation in BRG1 subunit may be assayed before or after amplification using one of several hybridization-based methods known in the art. Typically, allele-specific oligonucleotides are utilized in performing such methods. The allele-specific oligonucleotides may be used as differently labelled probe pairs, with one member of the pair showing a perfect match to one variant of a target sequence and the other member showing a perfect match to a different variant. Preferably, the members of the set have melting temperatures within 5 Degrees centigrade and more preferably within 2 degrees centigrade, of each other when hybridizing to each of the polymorphic or mutant sites being detected. Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking, baking, etc. Allele-specific oligonucleotide may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibres, chips, dishes, and beads. The solid support may be treated, coated or derivatised to facilitate the immobilization of the allele-specific oligonucleotide or target nucleic acid.

Polypeptides harboring a BRG1 mutation can also be assayed using methods known in the art, such as radioimmunoassays or enzyme-linked immunoassays, competitive binding enzyme-linked immunoassays, immunohistochemistry, mass spectrometry, ELISA, point of care techniques/platforms, dot blot, Western blot analysis, chromatography, preferably high performance liquid chromatography (HPLC), or the like. Labeled antibodies, binding portions thereof, or other binding partners can be used. The antibodies can be monoclonal or polyclonal in origin, or may be biosynthetically produced. The binding partners may also be naturally occurring molecules or synthetically produced. The amount of complexed proteins is determined using standard protein detection methodologies described in the art. A detailed review of immunological assay design, theory and protocols can be found in numerous texts in the art, including Practical Immunology, Butt, W. R., ed., Marcel Dekker, New York, 1984.

A variety of different labels can be used in the assays of the invention including direct labels such as fluorescent or luminescent tags, metals, dyes, radionucleides, and the like, attached to the antibody. Indirect labels include various enzymes well known in the art, such as alkaline phosphatase, hydrogen peroxidase and the like. In a one-step assay, the target protein (i.e., a BRG1 mutation) is immobilized and incubated with a labeled antibody. The labeled antibody binds to the immobilized target molecule. After washing to remove unbound molecules, the sample is assayed for the presence of the label. Numerous immunohistochemical methods are incorporated into point-of-care formats and hand-helds, all of which may be used for determine presence of the protein.

The use of immobilized antibodies specific for the proteins or polypeptides is also contemplated by the present disclosure. The antibodies can be immobilized onto a variety of solid supports, such as magnetic or chromatographic matrix particles, the surface of an assay place (such as microtiter wells), pieces of a solid substrate material (such as plastic, nylon, paper), and the like. An assay strip can be prepared by coating the antibody or a plurality of antibodies in an array on solid support. This strip can then be dipped into the test sample and processed through washes and detection steps to generate a measurable signal, e.g., a colored spot.

In a two-step assay, an immobilized target protein (e.g., a sample of lysate from a cancer cell harboring a BRG1 mutation) may be incubated with an unlabeled antibody. The unlabeled antibody complex, if present, is then bound to a second, labeled antibody that is specific for the unlabeled antibody. The sample is washed and assayed for the presence of the label. The choice of marker used to label the antibodies will vary depending upon the application. However, the choice of the marker is readily determinable to one skilled in the art.

Dot blotting is routinely practiced by the skilled artisan to detect a desired protein using an antibody as a probe (Promega Protocols and Applications Guide, Second Edition, 1991, Page 263, Promega Corporation). Samples are applied to a membrane using a dot blot apparatus. A labeled probe is incubated with the membrane, and the presence of the protein is detected.

Western blot analysis is well known to the skilled artisan (Sambrook et al., Molecular Cloning, A Laboratory Manual, 1989, Vol. 3, Chapter 18, Cold Spring Harbor Laboratory). In Western blotting, the sample is separated by SDS-PAGE. The gel is transferred to a membrane. The membrane is incubated with labeled antibody for detection of the desired protein.

Kits

The invention further provides kits for determining whether a BRG1 mutation exists in a sample taken from a subject, e.g., a BRG1 mutation in Table 1. The kits are useful for selecting patients who will specifically benefit from treatment with one or more BRM inhibitors. A kit can comprise primers and/or probes useful for detecting one or more BRG1 mutations. A kit may further comprise nucleic acid controls, buffers, and instructions for use. A kit can also comprise reagents and instructions for detecting loss of BRG1 expression. A kit can also comprise reagents and instructions for detecting loss of BRG1 function, e.g., through Western blotting, ELISA, immunohistochemistry, or similar techniques. A kit can also comprise reagents and instructions for confirming maintenance of BRM function and expression notwithstanding BRG1 mutation, loss of function, and/or loss of expression.

One skilled in the art will recognize many methods and materials similar or equivalent to those described herein, which could be used in the practice of the present invention. Indeed, the present invention is in no way limited to the methods and materials described.

EXAMPLES

Example 1: Pooled shRNA Screen to Identity Epigenetic Regulators Required for Cancer Cell Proliferation To identify genes involved in epigenetic regulation that are essential for viability of human cancer cells, we screened a deep coverage shRNA library (17 shRNAs per gene) targeting epigenetic regulators for effects on proliferation in a panel of 50 cell lines from the Cancer Cell Line Encyclopedia as described above.

Utilizing the RSA algorithm statistic to calculate the log p-value for each cancer cell line used in the screen, non-small cell lung cancer lines NCI-H838, NCI-H1299, A549, and HCC-15, which harbor BRG1 mutations, were shown to have log p-values −7.90, −11.6, −13.27, and −13.45, respectively, corresponding to statistically significant growth inhibition following inhibition of BRM function by shRNA mediated knockdown (data for the screen are shown in Table 4 and summarized visually in FIG. 1a). Similarly, the BRG1 mutant liver cancer line SK-HEP-1 and the ovarian cancer cell line TYK-nu with loss of BRG1 expression have log p-values of −14.92 and −10.9 respectively corresponding to statistically significant growth inhibition following inhibition of BRM function by shRNA mediated knockdown. The BRG1 mutant pancreatic cell line KP-1NL shows a more modest but statistically significant growth effect with log p-value of −4.28 consistant with BRM inhibition also inhibiting growth of pancreatic cancers with BRG1 loss of function cuased by BRG1 mutation or loss of BRG1 expression.

In contrast, the other cancer cell lines, whose p-values did not exceed −3 are not sensitive to BRM shRNAs. These results demonstrate the sensitivity of a subset of cancer cell lines with BRG1 loss of function due to either BRG1 mutation or loss of BRG1 expression from a range of lineages including lung, liver, and ovarian cancers show inhibition of cell growtn following inhibition of BRM activity following knockdown of BRM by shRNA. It is also important to note in this table that many of the BRG1 mutant lines also show low BRG1 expression (below 0.4) demonstrating that detection of BRG1 expression levels in cancer samples is a reliable marker for sensitivity of cancers to BRM inhibition.

TABLE 4

Summary of pooled shRNA data documenting growth inhibition in BRG1 mutant cell lines in response to BRM knockdown.

| Cell Line | Log p-value (RSA) | Sensitive by K-means | BRG1 Expression | Description of Mutation | Primary Site |
| --- | --- | --- | --- | --- | --- |
| SK-HEP-1 | −14.92 | Sensitive | 0.2575 | Homozygous p.E1582* | liver |
| HCC-15 | −13.45 | Sensitive | 0.34 | Homozgyous p.P269fs | lung |
| A549 | −13.29 | Sensitive | 0.21125 | Homozgyous p.L728fs | lung |
| NCI-H1299 | −11.96 | Sensitive | 0.29625 | p.K578fs, p.T560* | lung |
| NCI-H838 | −10.37 | Sensitive | 0.5825 | Homozygous p.I873_splice | lung |
| TYK-nu | −10.21 | Sensitive | 0.36125 | Lacks BRM expression | ovary |
| KP-1NL | −5.85 | Insensitive | 0.25875 | Lacks BRM expression | pancreas |
| HMC-1-8 | −4.60 | Insensitive | 1.01625 | Wild Type | breast |
| HGC-27 | −4.12 | Insensitive | 2.485 | Wild Type | stomach |
| A2058 | −2.77 | Insensitive | No Data | Wild Type | skin |
| BT-549 | −2.41 | Insensitive | 1.275 | Wild Type | breast |
| HCC1806 | −2.32 | Insensitive | 1.16375 | Wild Type | breast |
| A-498 | −2.31 | Insensitive | 0.8475 | Heterozygous p.A923P | kidney |
| KMRC-20 | −2.04 | Insensitive | 0.52375 | Wild Type | kidney |
| RMG-I | −1.87 | Insensitive | 0.70375 | Wild Type | ovary |
| Pa-Tu-8988T | −1.85 | Insensitive | No Data | Wild Type | pancreas |
| GP2d | −1.78 | Insensitive | 1.13375 | Heterozgyous p.I879V | large intestine |
| JHH-7 | −1.69 | Insensitive | 1.4625 | Wild Type | liver |
| Hey-A8 | −1.67 | Insensitive | 0.63875 | Wild Type | ovary |
| A2780 | −1.59 | Insensitive | 1.80375 | Heterozygous p.T910M | ovary |

TABLE 4-continued

Summary of pooled shRNA data documenting growth inhibition
in BRG1 mutant cell lines in response to BRM knockdown.

| Cell Line | Log p-value (RSA) | Sensitive by K-means | BRG1 Expression | Description of Mutation | Primary Site |
|---|---|---|---|---|---|
| HCT116 | −1.56 | Insensitive | 0.8475 | Heterozygous p.Y120fs, p.L1163P | large intestine |
| U-251 MG | −1.50 | Insensitive | 0.8675 | Wild Type | central nervous system |
| RMUG-S | −1.47 | Insensitive | 0.44 | Heterozygous Deletion | ovary |
| HEC-50B | −1.47 | Insensitive | No Data | Wild Type | endometrium |
| JHOM-1 | −1.45 | Insensitive | 0.7175 | Wild Type | ovary |
| HEC-151 | −1.45 | Insensitive | 1.0075 | Heterozygous T910M | endometrium |
| OVTOKO | −1.35 | Insensitive | 0.605 | Wild Type | ovary |
| HMCB | −1.32 | Insensitive | 1.5925 | No Sequence Information available | skin |
| G-401 | −1.30 | Insensitive | 2.13125 | Wild Type | soft tissue |
| KP4 | −1.25 | Insensitive | 0.3675 | Lacks BRG1 expression | pancreas |
| SNU-449 | −1.23 | Insensitive | No Data | Wild Type | liver |
| MIA PaCa-2 | −1.18 | Insensitive | 1.90625 | Wild Type | pancreas |
| LS411N | −1.11 | Insensitive | 0.915 | Wild Type | large intestine |
| Hep3B | −1.11 | Insensitive | No Data | Wild Type | liver |
| VMRC-RCW | −1.08 | Insensitive | 0.63 | Heterozygous p.P647L | kidney |
| H4 | −0.99 | Insensitive | No Data | Wild Type | central nervous system |
| SW480 | −0.95 | Insensitive | 0.60625 | No Sequence Information available | large intestine |
| JHOS-2 | −0.83 | Insensitive | 0.5825 | Wild Type | ovary |
| RD | −0.75 | Insensitive | 2.24875 | Wild Type | soft tissue |
| ES-2 | −0.70 | Insensitive | 0.94 | Wild Type | ovary |
| PC-14 | −0.68 | Insensitive | 0.855 | Wild Type | lung |
| RKO | −0.67 | Insensitive | 0.7025 | Wild Type | large intestine |
| COR-L23 | −0.62 | Insensitive | 1.3075 | Heterozygous p.K689del | lung |
| KNS-62 | −0.58 | Insensitive | 0.68875 | Wild Type | lung |
| Ishikawa (Heraklio) 02 ER- | −0.57 | Insensitive | No Data | Wild Type | endometrium |
| HuH-7 | −0.48 | Insensitive | 1.13 | Wild Type | liver |
| KYSE-150 | −0.48 | Insensitive | 0.80875 | Heterozygous p.N944K | oesophagus |
| LCLC-103H | −0.46 | Insensitive | 0.74875 | Wild Type | lung |
| TOV-21G | −0.46 | Insensitive | 1.5175 | Wild Type | ovary |
| HT-29 | −0.43 | Insensitive | 0.87 | Wild Type | large intestine |
| 786-O | −0.43 | Insensitive | 1.3275 | Wild Type | kidney |
| HPAC | −0.40 | Insensitive | 0.83 | Wild Type | pancreas |
| JHUEM-1 | −0.33 | Insensitive | 1.01375 | Heterozygous p.S1176N | endometrium |
| HCC-44 | −0.32 | Insensitive | 0.895 | Wild Type | lung |
| LK-2 | −0.31 | Insensitive | 1.73375 | Wild Type | lung |
| OVISE | −0.27 | Insensitive | 1.3275 | Wild Type | ovary |
| JMSU-1 | −0.25 | Insensitive | 2.34625 | Wild Type | urinary tract |
| SBC-5 | −0.24 | Insensitive | 0.35 | Lacks BRG1 and BRM | lung |

Methods

Library Design & Construction. A custom 6,500 element shRNA library focused on enzymes involved in epigenetic regulation was constructed using chip based oligonucleotide synthesis and cloned as a pool into the BpiI site of the pRSI9 lentiviral plasmid (reference Cellecta). The shRNA library targeted 384 genes (Table 4) with an average of 17 unique shRNAs/gene. The shRNA includes 2 G/U mismatches in the passenger strand, a 7 nucleotide loop, and a 21 nucleotide targeting sequence. Targeting sequences were designed using a proprietary algorithm (Cellecta). The oligo corresponding to each shRNA was synthesized with a unique 18 nucleotide barcode for measuring representation by NGS. Sequencing of the plasmid pool showed excellent normalization (FIG. 1B) with >90% clones present at a representation of +/−5-fold from the median counts in the pool.

Viral Packaging, transduction and screening. 12,000 293T cells per plate were plated on multiple collagen coated 150 mm plates 24 hrs prior to transfection. Cells were transfected according to the manufactures recommended protocol (ref). For each 150 mm plate, cells were transfected using 24.3 uL of TransIT reagent diluted 875.7 uL of OPTI-MEM that was combined with 3.6 ug of the plasmid pool and 4.5 ug of the Cellecta packaging mix (containing the psPAX2 and pMD2 plasmids that encode Gag/Pol and VSV-G respectively). Virus was harvested at 72 hrs post transfection, aliquoted, and frozen at −80 C for later use. Viral titer was measured by infecting HCT116 cells with a 10-point viral dose response curve and measuring the percentage infected cells by monitoring expression of the RFP expression casset that is part of the viral construct by FACS. Typical viral titers were in the range of 1-5×10$^6$ TU/mL using this procedure.

For each cell line the optimal puromycin dose required to achieve >95% cell killing in 72 hrs was determined by measuring cell viability with a Cell TiterGlo assay for a 6-point dose response ranging from 0 to 5 ug puromycin. The volume of virus required to give an MOI of 0.3 was determined using a 10 point dose response ranging from 0 to 400 uL of viral supernatant in the presence of 8 ug/mL polybrene. Infectivity was determined as the % RFP positive cells as measured by FACS.

Screens were run in duplicate. For large-scale infections, 24-million cells were plated 24 hrs prior to infection in T-175 flasks (typical cell densities were between 2-8 million cells/flask). On the day of infection, the culture media was replaced with fresh media containing 8 ug/mL polybrene and sufficient virus was added to give an MOI of 0.3 was added. 24 hrs after infection, the culture media was replaced with fresh media containing puromycin. 72 hrs following puromycin addition, cells were trypsinized, and 24 million cells were plated into new flasks. An aliquot of cells was used to measure transduction efficiency determined by measuring the % RFP positive cells and was typically >90%. Cells were maintained in culture and split as needed to ensure they did not exceed 90% confluence during the course of the screen. At each split, 24 million cells were passaged into new flasks, ensuring a representation of >1000 cells/shRNA in the library and the % RFP positive cells was measured to ensure stability of the transduced population over time. When the cells reached 5-population doublings, 40 million cells were harvested by centrifucation and stored at −20° C.

Purification of Genomic DNA & PCR for Library production. 20 million cells were resuspended in PBS according to the DNeasy protocol (Qiagen) at 200 ul PBS per 5 million cells. This resuspension is then aliquoted at 200 ul (5e6 cells) into 4×1.5 ml tubes, treated with ProteinaseK, RNaseA and Buffer AL and are incubated for lysis, and processed for gDNA isolation as directed. The final DNA concentration is assayed using Picogreen reagent giving a tyipcal yield of 1 ug gDNA per million cells.

For NGS library generation, the barcodes are amplified in 8×50 uL PCR reactions using 1 ug of gDNA per reaction with Titanium Taq and Primers #3323 (PEFwdGEX), #3324 (PECellectaA), #3197-3223 (one of 27 indexing oligos; see PCR scheme in FIG. 1C) for 28 cycles. The product was analyzed by agarose gel electrophoresis to check for the expected ~120 bp product and purified using the Agencourt. AMPure XP PCR cleanup kit (Beckman Coulter) and the amount of purified product quantified using a Picogreen DNA concentration assay. Barcode representation was measured by Next Generation Sequencing on an Illumina GA2× system.

Data Analysis. Counts from each sample were normalized to 16 million reads. The number of reads observed for each barcode at 5-population doublings was divided by the number of reads for the corresponding barcode in the original plasmid pool to give the fold change in representation during the experiment. A robust z-score was calculated using the median and MAD for the fold change in counts across the entire shRNA library. The deep coverage shRNA libraries used in this work enable high confidence hit calling at the gene level, rather than analysis of individual shRNAs in the data set. For gene based hit calling, two statistical measures were used, (1) Redundant siRNA Activity or RSA (ref), and (2) Q1 Z-score. To identify statistically significant correlations between shRNA sensitivity and genetic features of the cell lines, we first performed a k-means clustering for the RSA value for a particular gene across all the cell lines screened to identify groups of 'sensitive' and 'in-sensitive' cell lines. This partition was then used to calculate the statistical significance of the co-occurance of all genetic features in the COLE data set (ref COLE paper).

Cell Culture

NCI-H1299, NCI-H460 and NCI-H838 were cultured in RPMI1640 medium (Lonza, #12-115Q) containing 10% FBS (Thermo Hyclone, #SH30071.03) and A549 cells were cultured in DMEM (with high glucose and sodium pyruvate) (Lonza, #12-604F) containing 10% FBS. BEAS2B cells were cultured in bronchial epithelial cell growth medium (Lonza, #CC-3170).

Western Blotting

Cells were harvested in lysis buffer containing 20 mM Tris-HCl (pH 7.5) 150 mM NaCl, 1 mM Na(2)EDTA, 1 mM EGTA, 1% Triton, 2.5 mM Sodium Pyrophosphate, 1 mM β-Glycerophosphate, 1 mM Na$_3$VO$_4$, 1 μg/mL Leupeptin and 1 mM PMSF (Cell signaling #9803). 10-20 μg of protein was loaded onto a gradient Bio-Rad 4-15% polyacrylamide gel. Protein was transferred onto a PVDF membrane (Bio-RAD, #170-4157) at 25v for 10 min. Membrane was blocked in 4% milk or Starting Block Blocking Buffers (Thermo Scientific, cat #37543). Antibodies used include anti-BRM (Cell Signaling Technology (CST #6889) at a 1:500-1000 dilution in blocking buffer overnight at 4° C., anti-BRG1 (CST #3508) was used at 1:500-1000 in blocking buffer overnight at 4° C., anti-β-Tubulin(Santa Cruz Biotech, #SC-5274) was used at 1:2000 overnight at 4° C., and anti-Vinculin (Sigma #v9131) was used at 1:2000 overnight at 4° C. Secondary antibody goat anti-rabbit IgG-HRP, (Santa Cruz Biotech #SC-2030) was used at, 1:5000, 90 min room and chemiluminescent signal was detected using SuperSignal West Femto Maximum Sensitivity Substrate, (Pierce, Cat #34095).

Generation of Inducible shRNA Constructs shRNA sequences were designed to include EcoRI and AgeI restriction sites to allow subsequent cloning into the pLKO-Tet-On inducible vector system. The sequences for the oligos used are as follows with the sense sequence in bold and the antisense sequence in lower case. The CTCGAG stem loop was used for sh2025 and sh5537, whereas the cellecta stem loop sequence GTTAATATTCATAGC was used for the top oligo, and GCTATGAATATTAAC for the bottom oligo for cellecta based shRNAs 631, 1738, 4492 and 4493. The sequences of the oligonucleotides used are as follows from 5' to 3':

```
Non-targeting control (CTL)
shRNA sequence (top and bottom oligos):
                                      (SEQ ID NO: 1)
CCGGGGATAATGGTGATTGAGATGGCTCGAGccactcaatcaccattatc cTTTTT;

(SEQ ID NO: 2)
AATTAAAAAGGATAATGGTGATTGAGATGGCTCGAGccactcaatcacca ttatcc

BRM sh2025
                                      (SEQ ID NO: 3)
CCGGGAAGAGAGTGATTCTGATTATCTCGAGataatcagaatcactctct tcTTTTT;

(SEQ ID NO: 4)
AATTAAAAAGAAGAGAGTGATTCTGATTATCTCGAGataatcagaatcac tctcttc;

BRM sh5537
                                      (SEQ ID NO: 5)
CCGGGTTGAAAGCGCTATTGAATATCTCGAGatattcaatagcgctttca acTTTTT;

(SEQ ID NO: 6)
AATTAAAAAGTTGAAAGCGCTATTGAATATCTCGAGatattcaatagcgc tttcaac;

Cellecta BRM shRNA 631
                                      (SEQ ID NO: 7)
CCGGCGACTCTATCTAACTGGATATGTTAATATTCATAGCatgtccagtt agatagagtcgTTTTTT;
```

-continued

Cellecta BRM shRNA 1738

(SEQ ID NO: 8)
AATTAAAAAACGACTCTATCTAACTGGATATGCTATGAATATTAACatgt ccagttagatagagtcg;

Cellecta BRM shRNA 1738

(SEQ ID NO: 9)
CCGGCCAAACTTGTAGTGAGTGATTGTTAATATTCATAGCaatcgctcac tacaggtttggTTTTTT;

(SEQ ID NO: 10)
AATTAAAAAACCAAACTTGTAGTGAGTGATTGCTATGAATATTAACaatc gctcactacaggtttgg;

Cellecta BRM shRNA 4492

(SEQ ID NO: 11)
CCGGGACAGGTGTTTAGCTTACTTTGTTAATATTCATAGCaaggtaagct aaacgcctgtcTTTTTT;

(SEQ ID NO: 12)
AATTAAAAAAGACAGGTGTTTAGCTTACTTTGCTATGAATATTAACagg taagctaaacgcctgtc;

Cellecta BRM shRNA 4493

(SEQ ID NO: 13)
CCGGGCAGCTAAAGAGAAGAAGAGGGTTAATATTCATAGCcttcttcttc tctttggctgcTTTTTT;

(SEQ ID NO: 14)
AATTAAAAAAGCAGCTAAAGAGAAGAAGAGGGCTATGAATATTAACcttc ttcttctctttggctgc.

BRG1 shRNA 2202

(SEQ ID NO: 15)
CCGGGCCAAGCAAGATGTCGATGATCTCGAGatcatcgacatcttgcttg gcTTTTT (SEQ ID NO: 16)
AATTAAAAAGCCAAGCAAGATGTCGATGATCTCGAGatcatcgacatctt gcttggc 11.25 ul of each the top and bottom oligonucleotides (0.1 nmole/μl) and 2.5 ul 10× annealing buffer (1 M NaCl, 100 mM Tris-HCl, pH 7.4) were annealed at 95° C. for 4 min followed by a 10 min incubation at 24° C. in a thermo cycler. Annealed oligos were subsequently diluted at 1:400 in 0.5× annealing buffer, and 1 μl was used in a T4 DNA ligase reaction together with gel-purified EcoRI/AgeI digested pLKO-Tet-On vector. Transformation was done in one shot Stb13 competent E. coli cells (Invitrogen, #C7373-03) and selected clones were digested with XhoI to verify presence of insert. Positive clones were confirmed by sequencing using the following sequencing primer 5' GGCAGGGAT-ATTCACCATTATCGTTTCAGA3' (SEQ ID NO:17).

Production of Lentiviral Supernatants for the Inducible shRNA constructs. Early passage 293T cells were seeded at 2.4-4×10^6 cells on BD BioCoat™ Collagen I 100 mm Culture Dishes (BD Biosciences, #354450). Cells were transfected with lenti viral packaging plasmids (2.4 μg Δ8.9 and 0.6 μg of VSVG) with 2.4 μg of shRNA construct using the TransIT-293 transfection reagent (Miris, #MIR 2700). Medium was replaced 24 hours following transfection and viral supernatants were harvested at 24 and 36 hr. Viral supernatants were pooled and filtered through 0.45 uM cellulose acetate filters (corning, #430314).

Lentiviral Infection of Lung Cancer Cell Lines. Lentiviral infection of lung cancer cell lines was performed by plating 100,000 cells in a 6 well plate, and infecting the next day with 1 mL of lentiviral supernatant in the presence of polybrene (8 μg/mL). Cells were spinfected for 1 hour (800 G) at room temperature. Medium was replaced the following day and stable pools of cells were selected with 800 ng/mL of neomycin.

Growth and Focus Formation Assays. 500-750 Cells were seeded in 96 well plates in triplicate. Cells were either untreated or treated with 100 ng/mL Doxycycline (Clontech, #631311) immediately after plating and then replenished every other day. Cell viability was measured using Cell Titer Glo (Promega, G7573) at various time points. Focus formation assays were carried out by seeding 1000 cells/well of a 6 well plate in triplicate and treating with either 0 or 100 ng/mL of Dox right after plating and continuing treatment with Dox every 2-3 days. After 10-14 days, colonies were visualized by staining with crystal violet.

Cell Cycle Analysis. Cells were trypsinized, washed with 1 ml of PBS and fixed in 70% ethanol overnight at 4° C. After 2 washes with 1 ml of PBS, cells were resuspended in PBS containing 33 μg/ml propidium iodide and 200 μg/ml RNAse A for 30 min at 37° C. Flow cytometry was performed on a BD FACSCanto cytometer and analyzed with FloJo software (Tree Star).

Senescence Assays. Senescence-associated β-Galactosidase activity was monitored with the Senescence β-Galactosidase Staining Kit (Cell Signaling, #9860) according to the manufacturer's instructions.

Immunofluorescence. Cells were grown in the presence or absence of doxycyline for the indicated times on collagen I coated chamber slides (BD, 354630) and fixed with 3.7% formaldehyde for 10 min. Primary antibodies were incubated overnight at 4° C. at a 1:1000 dilution; secondary antibodies were incubated for 1 hr at room temperature at a 1:1000 dilution; DAPI (1 ug/ml) was used to stain nuclei. The following primary antibodies were used rabbit anti-trimethyl histone 3 (Lys9) (Millipore; 07-442). Donkey anti-rabbit Alexa488 (Life Technologies; #A-21206) or anti-rabbit Alexa568 (Life Technologies; #A10042) were used as secondary antibodies.

RNA Extraction and Quantitative RT-PCR. HCT116 cells were seeded in 96 well plates (1000-1500/well in triplicate), and subsequently infected with 15 ul of lentivirus with 8 ng/mL polybrene and spin infected at 800 G for 1 hour at room temperature. 24 hours after infection, cells were selected with 1.5 mg/mL neomycin for 3 days, and subsequently treated with 0 or 100 ng/mL of dox for 2 days to induce expression of shRNAs. After 48 hours of Dox treatment, plates were washed with cold PBS, then lysed with 50 μl lysis buffer provided in the Taqman gene expression Cells-to-Ct kit (Applied biosystems, #4399002). After adding stop solution, 12.5-22.5 μl lysates were used for cDNA synthesis in the present of RT buffer and enzyme (total volume of 50 μl) provided by the kit. 2-4 μl cDNA was then used for ABI taqman gene expression assay in total reaction 12 μl by ABI PRISM 7900 HT Sequence Detection System (Applied Biosystems, ABI). ABI taqman gene expression assays include: VIC-MGB β-actin primers/probe (Applied Biosystems), BRM Gene expression assay, Hs00268234_ml were used in each reaction to co-amplify the β-actin transcript. All experiments were performed in triplicate and normalized to β-actin levels. Relative mRNA expression is given by the formula $2^{-(C_T \text{ of sample} - C_T \text{ of } \beta\text{-actin})}$, where $C_T$ (cycle count) is the threshold cycle value.

RNA Extraction and Quantitative RT-PCR for Selected Top Up/Down Regulated Genes from Transcriptional Profiling Experiments Cells were plated at 0.1-0.15×10^6/well in six well plates and treated with or without doxycycline (100 ng/mL) for 2, 3 and 4 days. Cells were then washed with ice cold PBS and lysed with 350 uL Buffer RLT (+1% B-Mercaptoethanol) provided in the RNeasy Mini Kit (Qiagen #74106). Lysate was homogenized using QIAshredder (Qiagen #79654) and On-column DNase digestion was performed with RNase-Free DNase Set (Qiagen #79254) according to manufacturer's instructions. Samples were applied to an RNeasy Mini spin column containing a silica-based membrane provided by the RNeasy Mini Kit (Qiagen #74106). After washing, RNA was eluted in 50 uL RNase free ddH2O and concentration was measured using Nanodrop ND-8000 8-Sample Spectrophotometer. cDNA was synthesized from total RNA using iScript cDNA synthesis Kit (BioRad #170-8891). 0.5-1.5 μg total RNA was added in a total volume of 20 μL containing 5 μL iScript reverse transcription supermix (Bio-Rad #170-8841).

The reaction was primed 5 min with 25° C., and reverse transcription was performed for 30 min at 42° C. and reverse transcription was inactivated with 5 minutes incubation at 85° C. Obtained cDNA was diluted 1:10 in ddH2O and 4 μL used for quantitative PCR in a total reaction volume of 10 μL and triplicates. Mastermix was prepared with 6 μL of Fast-Start Universal Probe Master (Rox) (Roche #04914058001) and 0.6 μL either with 20× probe/primer mix (ABI) or probe/primer mix (IDT) containing 5 μM probe and 10 μM of each primer forward and reverse. qPCR was performed in a 384 well plate using the 7900HT Fast Real-Time PCR System (Applied Biosystems). Level of mRNA was normalized to the housekeeping gene human beta actin which was detected in a separate reaction.

In Vivo Efficacy Studies. Female athymic nude mice (Harlan) were acclimated in Novartis Institutes for BioMedical Research animal facility (12 hour light/dark cycle) with ad libitum access to food and water for at least 3 d before manipulation. All animal studies were carried out according to the Novartis Guide for the Care and Use of Laboratory Animals. Mice (6-8 wk old, n=8) were inoculated subcutaneously in the right dorsal axillary region with NCI-H1299 ($10 \times 10^6$ cells in 200 ul HBSS) or NCI-H640 ($5 \times 10^6$ cells in 200 ul HBSS) cancer cells stably expressing dox-inducible control (CTL) nontargeting shRNA or two distinct BRM-targeting shRNAs (sh2025 or sh5537). Tumor volume was measured twice weekly by calipering in two dimensions and calculated as (width$^2$×length×π/6). When average tumor volume reached approximately 250 mm$^3$, animals were randomly assigned to receive either vehicle diet (standard diet) or doxycyxline supplemented diet (Mod LabDiet® 5053, 400 ppm doxycycline) for the duration of the study. At termination of each study, tumor tissue was collected from each group and snap frozen in liquid nitrogen or fixed overnight in 10% formalin. To evaluate early knock down and pharmacodynamic effects, a separate set of tumor bearing animals (n=3/group) was administered vehicle or doxycycline diet for 7 consecutive days after which tumor tissue was excised and snap frozen in liquid nitrogen or fixed in 10% neutral-buffered formalin.

Immunohistochemistry and image analysis. Xenograft tumor samples were fixed in 10% neutral-buffered formalin for approximately 24 hours, processed, and paraffin embedded. Immunohistochemical staining was performed on the Ventana Discovery System. Primary antibodies used are BRG1 from Abcam (ab108318); BRM from Cell Signaling (6889); E-cadherin from Cell Signaling (3195); Ki67 from Vector Laboratories (clone SP6, VP-RM04); and vimentin from Cell Signaling (5741). Images of whole tumor sections were captured using Aperio Scanscope and analyzed with ImageScope (Aperio Technologies, Vista, Calif.) and the Visiopharm Integrator System (V.4.4.4.0; Visiopharm, Hørsholm, Denmark). Stromal tissue and necrotic regions were manually excluded using the drawing tools provided by the analysis software platforms. Tissues were segmented using the TissuemorphDP module. DAB intensity was quantified as percent positive nuclei.

Alcian blue staining. Xenograft tumor samples were fixed in 10% neutral-buffered formalin for approximately 24 hours, processed, and paraffin embedded. FFPE sections were cut at 5 μM, mounted on slides, baked at 60° C. for at least 30 minutes, and deparaffinized. Slides were then rinsed two times in H$_2$O, transferred to Acetic Acid 3% Aqueous for 3 minutes, and moved directly to Alcian Blue 1% in 3% Acetic Acid pH 2.5 for 30 minutes. Slides were then placed in running water for 10 minutes after which they were rinsed in dH2O before being placed in Nuclear Fast Red 0.1% (Kernechtrot) for 5 minutes. Slides were again washed in running water, and then dehydrated. Lastly, the slides were coverslipped with Permaslip.

Statistical analysis. Unpaired t tests were used to determine statistical significance. For the tumor growth inhibition studies, statistical analysis was performed on delta tumor volume (final tumor volume minus starting tumor volume). Symbols used: *P<0.05; P<0.01; *P<0.001; ns, not significant.

We claim:

1. A method of treating a subject afflicted with a cancer associated with one or more BRG1 mutations comprising the steps of:
   a) contacting a sample obtained from said subject with a reagent capable of detecting human cancer cells harboring one or more BRG1 mutations or loss of BRG1 expression;
   b) comparing the sample obtained from said afflicted subject with a similar sample taken from a non-cancerous or normal control subject, wherein the presence of one or more BRG1 mutations in said sample obtained from said afflicted subject indicates said afflicted subject will respond to therapeutic treatment with a BRM inhibitor; and
   c) administering a therapeutically effective amount of BRM inhibitor to those subject identified in step b) wherein the cancer is squamous cell lung carcinoma, non-small cell lung carcinoma, large cell lung carcinoma, lung adenocarcinoma, liver or ovarian cancer.

2. The method of claim 1, wherein the reagent capable of detecting human cancer cells harboring one or more BRG1 mutations or loss of BRG1 expression is an anti-BRG1 antibody.

3. A method of treating a subject afflicted with a cancer associated with one or more BRG1 mutations comprising the steps of:
   a) contacting a sample obtained from said subject with a reagent capable of detecting human cancer cells harboring one or more BRG1 mutations;

b) comparing the sample obtained from said afflicted subject with a similar sample taken from a non-cancerous or normal control subject, wherein the presence of one or more BRG1 mutations in said sample obtained from said afflicted subject indicates said afflicted subject will respond to therapeutic treatment with a BRM inhibitor; and c) administering a therapeutically effective amount of BRM inhibitor to those subject identified in step b) wherein the reagent capable of detecting human cancer cells harboring one or more BRG1 mutations is one or more PCR probes specific for one of the BRG1 mutations listed in Table 1 and Table 2.

4. The method of claim 3, wherein the BRM inhibitor is a short hairpin RNA (shRNA) or short inhibitory RNA (siRNAs).

5. The method of claim 3, wherein the BRM inhibitor is an antibody drug conjugate.

6. A method of treating a subject afflicted with a cancer associated with one or more BRG1 mutations comprising the steps of administering a therapeutically effective amount of a BRM inhibitor to the subject, wherein the cancer is squamous cell lung carcinoma, non-small cell lung carcinoma, large cell lung carcinoma, lung adenocarcinoma, liver or ovarian cancer.

7. The method of claim 6, wherein the BRM inhibitor is a short hairpin RNA (shRNA) or short inhibitory RNA (siRNAs).

8. The method of claim 6, wherein the BRM inhibitor is an antibody drug conjugate.

9. The method of claim 1, wherein the BRM inhibitor is a short hairpin RNA (shRNA) or short inhibitory RNA (siRNAs).

10. The method of claim 1, wherein the BRM inhibitor is an antibody drug conjugate.

11. The method of claim 3 wherein the cancer is squamous cell lung carcinoma, non-small cell lung carcinoma, large cell lung carcinoma, lung adenocarcinoma, liver or ovarian cancer.

12. The method of claim 6, wherein the BRM inhibitor is a short hairpin RNA (shRNA) or short inhibitory RNA (siRNAs).

13. The method of claim 6, wherein the BRM inhibitor is an antibody drug conjugate.

* * * * *